US007105161B1

(12) United States Patent
Gajewczyk et al.

(10) Patent No.: US 7,105,161 B1
(45) Date of Patent: Sep. 12, 2006

(54) PROTEINACEOUS ADJUVANTS

(75) Inventors: Diane M. Gajewczyk, Aurora (CA); Heather A. Boux, Victoria (CA); Anton Novak, Toronto (CA); Michel H. Klein, Willowdale (CA)

(73) Assignee: Sanofi Pasteur Inc., Swiftwater, PA (US)

( * ) Notice: Subject to any disclaimer, the term of this patent is extended or adjusted under 35 U.S.C. 154(b) by 0 days.

(21) Appl. No.: 08/750,378

(22) PCT Filed: Jun. 8, 1995

(86) PCT No.: PCT/CA95/00341

§ 371 (c)(1), (2), (4) Date: Oct. 31, 1997

(87) PCT Pub. No.: WO95/34323

PCT Pub. Date: Dec. 21, 1995

Related U.S. Application Data

(63) Continuation-in-part of application No. 08/258,228, filed on Jun. 10, 1994.

(51) Int. Cl.

| | |
|---|---|
| ***A61K 39/00*** | (2006.01) |
| ***A61K 39/38*** | (2006.01) |
| ***A61K 9/127*** | (2006.01) |
| ***A61K 39/02*** | (2006.01) |
| ***A61K 38/00*** | (2006.01) |
| ***A61K 38/16*** | (2006.01) |
| ***C07K 1/00*** | (2006.01) |

(52) U.S. Cl. ................ 424/184.1; 424/450; 424/236.1; 424/277.1; 424/254.1; 424/240.1; 514/2; 514/8; 530/350

(58) Field of Classification Search ............ 424/184.1, 424/234.1, 185.1, 203.1, 190.1, 236.1, 240.1, 424/239.1, 278.1, 282.1
See application file for complete search history.

(56) References Cited

U.S. PATENT DOCUMENTS

| | | | | |
|---|---|---|---|---|
| 5,085,862 | A | 2/1992 | Klein et al. | 424/92 |
| 5,182,109 | A | 1/1993 | Tamura et al. | 424/92 |
| 5,221,618 | A | 6/1993 | Klein et al. | 435/69.1 |
| 5,244,657 | A * | 9/1993 | Klein et al. | 424/88 |
| 5,332,583 | A * | 7/1994 | Klein et al. | |
| 5,358,868 | A * | 10/1994 | Klein et al. | |
| 5,773,600 | A * | 6/1998 | Burnette, III | 536/23.7 |
| 5,786,189 | A * | 7/1998 | Locht et al. | 424/200.1 |
| 5,932,714 | A * | 8/1999 | Loosmore et al. | |
| 5,942,418 | A * | 8/1999 | Loosmore et al. | |
| 6,109,982 | A * | 8/2000 | Okabe et al. | 439/748 |
| 6,140,082 | A * | 10/2000 | Loosmore et al. | |
| 6,861,410 | B1 * | 3/2005 | Ott et al. | 514/26 |
| 2003/0072774 | A1 * | 4/2003 | Gajewczyk et al. | 424/254.1 |
| 2003/0113345 | A1 * | 6/2003 | Clements | 424/203.1 |
| 2005/0158334 | A1 * | 7/2005 | Contorni et al. | 424/190.1 |
| 2005/0163746 | A1 * | 7/2005 | Karmon et al. | 424/85.1 |

FOREIGN PATENT DOCUMENTS

| | | |
|---|---|---|
| EP | 352250 | * 1/1990 |
| EP | 462534 | * 12/1991 |

OTHER PUBLICATIONS

Gajewczyk et al. FEMS Symposium No. 73, Bacterial Protein Toxins; 6th European Workshop, Stirling, Scotland, UK, Jun. 27-Jul. 2, 1993. J Freer et al (eds) New York, 1994.*
Boon, T. Scientific American. Mar. 1993, pp. 82-89.*
Munoz et al. Microbiol Immunol 33:341-355, 1989 (Abstract).*
Nencioni et al, Infection and Immunity, May 1990, 58/5:1308-1315.*
Lobet et al, Infection and Immunity, Nov. 1989, 57/11:3660-3662.*
Aprile et al, Canadian J. Public Health, 1966, 57:343-354.*
Nencioni et al, Infection and Immunity, Feb. 1991, 59/2:625-630.*
Tommaso et al, Infection and Immunity, Mar. 1996, 64/3:974-979.*
Partidos et al, Immunology, 1996, 89:483-487*
Lycke et al, Eur. J. Immunology, 1992, 22:2277-2281.*
Douce et al, PNAS, USA, Feb. 1995, 92:1644-1648.*
Podda et al, J. Exp. Med., Sep. 1990, 172:861-868.*
Burnette et al, Infection and Immunity, Nov. 1991, 59/11:4266-4270.*
Loosmore et al, Infection and Immunity, Jun. 1993, 61/6:2316-2324.*
Farizo et al, Infeection and Immunity, Jul. 2000, 68/7:4049-4054.*
Jobling et al, J. Bacteriology, Jul. 2001, 183/13:4024-4032.*
Yokomizo et al, Vet. Immunol. and Immunopathol., 2002, 87:291-300.*
Sanchez et al, JBC, Sep. 6, 2002, 277/36:33369-33377.*
Bartley et al, PNAS USA, Nov. 1989, 86:8353-8357.*
Bergstrand H., Andersson I., Nystrom I., Pauwels R., Bazin H. (1983) The Non-specific enhancement of allergy. II. Precipitation of anaphylactic *in vitro* response capacity and serum IgE and IgG2a antibody synthesis in primed but non-responding rats by injection of alum. Allergy 38:247-260.
Cogne M., Ballett J.J. Schmitt C., Bizzini B. (1985) Total and IgE antibody levels following booster immunization with aluminum adsorbed and nonadsorbed tetanus toxoid in humans. Ann. Allergy 54:148-151.

(Continued)

*Primary Examiner*—Nita Minnifield
(74) *Attorney, Agent, or Firm*—Sanofi Pasteur, Inc.

(57) ABSTRACT

A modulated immune response to an antigen is achieved by coadministering the antigen and a genetically-detoxified *pertussis* holotoxin, particularly one retaining its immunogenicity, to a host. The modulated immune response enables immunogenic compositions, including multivalent pediatric vaccines such as DTP, to be provided which produce a modulated immune response in the absence of extrinsic adjuvants such as alum. The adjuvanting effect achieved by the genetically-detoxified *pertussis* holotoxin enables at least the same level of adjuvanting effect to be achieved as previously attained by alum, without the undesirable side effects thereof.

10 Claims, 9 Drawing Sheets

OTHER PUBLICATIONS

Nagel J., Svec D., Waters T., Fireman P. (1977) IgE Synthesis in Man: I. Development of specific IgE antibodies after immunization with Tetanus-Diphtheria (Td) toxoids. J. Immunol. 118:334-341.

Hedenskog S., Bjorksten B., Blennow M., Granstrom G., Granstrom M. (1989) Immunoglobulin E response to pertussis toxin in whooping cough and after immunization with a whole cell and an acellular pertussis vaccine. Int. Arch. Allergy Appl. Immunol. 89:156-161.

Medical Research Council (1951) Br. Med. J. 2:1464-1472. (p. 1471).

Medical Research Council (1956) Br. Med. J. 2:454-462.

Medical Research Council (1959) Br. Med. J. 1:994-1000.

Fine P.E., Clarkson J.A. (1987) Reflections on the efficacy of pertussis vaccines. Rev. Infect. Dis. 9:866-883.

Kanai K. (1980) Japan's experience in pertussis epidemiology and vaccination in the past thirty years. Jpn. J. Med. Sci. Biol. 33:107-143.

Miller D.L. Alderslade R., Ross E.M. (1982) Whooping cough and whooping cough vaccine: the risks and benefits debate. Epidemiol. Rev. 4:1-24.

Romanus V., Jonsell R., Bergquist S.O. (1988) Pertussis in Sweden after the cessation of general-immunization in 1979. Pediatr. Infect. dis. 6:364-371.

Munoz J.J., Arai H., Bergman K., Sadowski P.L. (1981) Biological activities of crystalline pertussigen from *Bordetella pertussis*. Infect. Immun. 33:820-826.

Marwick C. (1988) Pertussis vaccines: Trials and Tribulations. JAMA 259:2057-2059.

Storsaeter J., Hallander H., Farrington C.P., Olin P., Molby R., Miller E. (1990) Secondary analyses of the efficacy of two acellular pertussis vaccines evaluated in a Swedish phase III trial. Vaccine 8:457-461.

Loosmore, S. Zealey, G., Cockle S. Boux, H., Chong, P., Yacoob, R. and Klein, M. (1993) Characterization of pertussis toxin analogs containing mutations in B-oligomer subunits. Infect. Immun. 61:2316-2324.

Lobet Y ., Cieplak W., Smith S.G., Keith J.M. (1989) Effects of mutations on enzyme activity and immunoreactivity of the S1 subunit of pertussis toxin. Infect. Immun. 57:3660-3662.

Loosmore S., Cockle S., Zealey G., Boux H., Cockle S., Radika K., Fahim R., Zobrist G., Yacoob R.K., Chong P., Yao F.L., Klein M. (1990) Engineering of genetically detoxified pertussis toxin analogs for development of a recombinant whooping cough vaccine. Infect. Immun. 58:3653-3662.

Nencioni L., Pizza M., Bugnoli M., DeMagistris T., Di Tomasso A., Giovannoni F., Manetti R., Marsili I., Matteucci G., Nucci D., Olivieri R., Pileri P., Presentini R., Villa L., Kreeftenberg J.G., Silvestri S., Tagliaube A., Rappuoli R. (1990) Characterization of generically inactivated pertussis toxin mutants: Candidates for a new vaccine against whooping cough. Infect. Immun. 58:1308-1315.

Burnette, W.N., Cieplak W., Mar V.L. Kaljot K.T., Sato H., Keith J.M. (1988) Pertussis toxin S1 mutant with reduced enzyme activity and a conserved protective epitope. Science 242: 72-74.

Pizza M., Covacci A., Bartolini A., Perugini M., Nencioni L., DeMagistris T., Villa L., Nucci D., Manetti R., Bugnoli M., Giovannoni F., Olivieri R., Barbieri J., Sato H., Rappuoli R. (1989) Mutants of pertussis toxin suitable for vaccine development. Science 246:497-499.

Podda A., Nencioni L., Demagistris M., Di Tomasso A., Bossu P., Nuti S., Pileri P., Peppoloni S., Bugnoli M., Ruggiero P., Marsili I., D'Errico A., Tagliabue A., Rappuoli R. (1990) Metabolic, humoral and cellular responses in adult volunteers immunized with the genetically inactivated pertussis toxin mutant PT-9K/129G. J. Exp. Med. 172:861-868.

Milis K.H.G., Barnard A., Watkins J., Redhead K. (1993) Cell-mediated immunity to *Bordetella pertussis*: Role of Th1 cells in bacterial clearance in a murine respiratory infection model. Infect. Immun. 61:399-410.

Redhead K., Watkins J., Barnard A., Mills K.H.G. (1993) Effective immunization against *Bordetella pertussis* respiratory infection in mice is dependent on induction of cell-mediated immunity. Infect. Immun. 61:3190-3198.

De Magistris M., Romano M., Nuti S., Rappuoli R., Tagliabue A. (1988) Dissecting human T cell responses against *Bordetella* species. J. Exp. Med. 168:1351-1362.

Gearing A.J.H., Bird C.R., Redhead K., Thomas M. (1989) Human cellular immune responses to *Bordetella pertussis* infection. FEMS Microbiol. Immunol. 47:205-212.

Tomoda T., Ogura H., Kurashige T. (1991) Immune responses to *Bordetella pertussis* infection and vaccination. J. Inf. Dis. 163:559-563.

Petersen J.W., Ibsen P.H., Bentzon M.W., Capiau C., Heron I. (1991) The cell mediated and humoral immune response to vaccination with acellular and whole cell pertussis vaccine in adult humans. FEMS Microbial. Immunol. 76:279-288.

Podda A., DeLuca E., Titone L., Casadel A., Cascio A., Peppoloni S., Volpini G., Marsili I., Nencioni L., Rappuoli R. (1992) Acellular pertussis vaccine composed of genetically inactivated pertussis toxin: Safety and immunogenicity in 12-to-24 and 2-to-4 month old children. J. Pediatr. 120:680-685.

Podda A., Nencioni L., Marsili I., Peppoloni S., Volpini G., Donati D., Di Tommaso A., De Magistris T., Rappuoli R. (1991) Phase I clinical trial of an acellular pertussis vaccine composed of genetically detoxified pertussis toxin combined with FHA and 69-kDa Vaccine 9:741-745.

Nencioni L., Volpini G., Peppoloni S., Bugnoli M., DeMagistris T., Marsili I., Rappuoli R. (1990) Properties of Pertussis toxin mutant PT-9K/129G after formaldehyde treatment. Infect. Immun. 59:625-630.

Marsili I., Pizza M., Giovannoni F., Volpini G., Bartalini M., Olivieri R., Rappuoli R., Nencioni L. (1992) Cellular pertussis vaccine containing a *Bordetella pertussis* strain that produces a nontoxic pertussis toxin molecule. Infect. Immunol. 60:1150-1155.

Ling S.S., Deforest A., Pennridge Pediatric Associates, Smith D.G., Lazaro C., Wassilak G.F. (1990) Longitudinal study of adverse reactions following Diphtheria-Tetanus-Pertussis vaccine in infancy. Pediatrics 85:294-302.

Butler N.R., Voyce M.A., Burland W.L., Hilton M.J. Advantages of aluminum hydroxide adsorbed combined diphtheria, tetanus, and pertussis vaccines for the immunization of infants. Br. Med. J. 1:663-666.

Aprile M.A., Wardlaw A.C. (1966) Aluminum compounds as adjuvants for vaccines and toxoids in man: A review. Can J. Pub. Health 57:343-354.

Pineau A., Durand C., Guillard O., Bureau B., Stalder J. (1992) Role of aluminum in skin reactions after diphtheria-tetanus-pertussis-poliomyelitis vaccination: An experimental study in rabbits. Toxicology 73:117-125.

Goto N., Akama K. (1982) Histopathological studies of reactions in mice injected with aluminum-adsorbed *tetanus toxoid. Microbiol. Immunol.* 26:1121-1132.

Erdohazi M., Newman R.L. (1971) Aluminum hydroxide granuloma. Br. Med. J. 3:621-623.

Bernier R.H., Frank J.A., Nolan T.F. (1981) Abscesses complicating DTP vaccination. Am. J. Dis. Child. 135:826-828.

Cox N.H., Moss C., Forsyth A. (1988) Cutaneous reactions to aluminum in vaccines: an avoidable problem. Lancet ii, 43.

Strom J. (1967) Further experience of reactions, especially of a cerebral nature, in conjunction with triple vaccination: A study based on vaccinations in Sweden 1959-1965. Br. Med. J.4:320-323.

Lione A. (1986) More on aluminum in infants. New England J. Med. 314:923.

Gupta R.K.7 Sharma S.B., Ahuja S., Saxena S.N. (1987) The effect of aluminum phosphate adjuvant on the potency of pertussis vaccine. J. Biol. Stand. 15:99-101.

Saroso J.S., Bahrawi W., Witjaksono 14,., Budiarso R.L.P., Brotowasisto B., Dewitt W.R., Gomez C.Z. (1978) A controlled field trial of plain and aluminum hydroxide adsorbed cholera vaccines Surabaya, Indonesia, during 1973-1975. Bull. WHO 56:619.

Collier L.H., Polakoff S., Mortimer J. (1979) Reactions and antibody responses to reinforcing doses of adsorbed and plain tetanus vaccines. Lanct i:1364.
Gupta R.K., Relyveld E.H. (1991 Adverse reactions after injection of adsorbed diphtheria-pertussis-tetanus (DPT) vaccine are not due only to pertussis organisms or pertussis components in the vaccine. Vaccine 9:699-702.
Granstrom M., Granstrom P., Gillenius P., Askelof P. (1985) Neutralizing antibodies to pertussis toxin in whooping cough. J. Infect. Dis. 151:646-649.
GB,A,2 217 600 (Nat Inst Health ;Kitasato Inst (JP)) Nov. 1, 1989 see the whole document .
Database Chemical Abstracts File Server STN Karlsruhe Abstract No. 113:169930, De Grave et al 'Enhancement of the Humoral Immunity Against HBSAG by Pertussis Toxin' & Meded.FAC. Landbouwwet.,Rijksuniv.Gent (1989),54 (4B ,1553-5 see abstract.
The Journal of Immunology, vol. 148, No. 5, Mar. 1, 1992 pp. 1506-1511, Person et al 'Pertussis Toxin-Induced Lymphocytosis is Associated With Alterations in Thymocyte Subpopulations' see the whole document.
FEMS Symposium.Bacterial Protein Toxins; Sixth European Workshop, No. 73, Jun. 27, 1993—Jul. 2, 1993 Stirling, Scotland, UK, pp. 504-505, Gajewczyk et al 'Pertussis Toxin-Mediated IGE Immunopotentiation' see the whole document.
Infection and Immunity, vol. 58, No. 11, Nov. 1990 pp. 3653-3662, Loosmore et al 'Engineering of Genetically Detoxified Pertussis Toxin Analogs for Development of a Recombinant Whooping Cough Vaccine' cited in the application see the whole document.
Science, vol. 246, Oct. 27, 1989 pp. 497-500, Pizza et al 'Mutants of Pertussis Toxin Suitable for Vaccine Development' cited in the application see the whole document.
GB,A,2 144 129 (Likhite Vilas V) Feb. 27, 1985 see example 11.
Infection and Immunity, vol. 63, No. 6, Jun. 1995 pp. 2100-2108, Roberts et al 'A Mutant Pertussis Toxin Molecule that Lacks ADP-Ribosyltransferase Activity,PT-9K/129G, is an Effective Mucosal Adjuvant for Intranasally Delivered Proteins' see the whole document.
W0,A,95 09649 (Medeva Holding BV ;Roberts Mark (GB)) Apr. 13, 1995 see the whole document.
N.A. Miitcheson, "The carrrier effect in the secondary response to hapten-protein conjugates", Eur. J. Immunol. 1.18 (1971) National Institute for Medical Research, London.
M. Ui, "The multiple Biological A ctivities of Pertussis Toxin", Pathogenesis and Immunity in Pertussis—Edited by A..C. Wardlaw and R. Parton, 1988—John Wiley & Sons Ltd.
Sekiya, Microbiol. Immunol. 77: 905-915, 1988.
Herbert et al., Dictionary of Immunology, pp. 98-99, & p. 187.

* cited by examiner

PROTEINACEOUS ADJUVANTS

REFERENCE TO RELATED APPLICATION

This application is a continuation-in-part of copending U.S. patent application Ser. No. 08/258,228 filed Jun. 10, 1994.

FIELD OF THE INVENTION

The present invention relates to the field of immunology and is particularly concerned with proteinaceous adjuvants., i.e. materials which modulate immune responses to an antigen.

BACKGROUND OF THE INVENTION

Vaccines have been used for many years to protect humans and animals against a wide variety of infectious diseases. Such conventional vaccines consist of attenuated pathogens (for example, polio virus), killed pathogens (for example, *Bordetella pertussis*) or immunogenic components of the pathogen (for example, diphtheria toxoid). Some antigens are highly immunogenic and are capable alone of eliciting immune responses. Other antigens, however, fail to induce, for example, a protective immune response or induce only a weak immune response.

Immunogenicity can be significantly improved if the antigens are co-administered with adjuvants. Adjuvants enhance the immunogenicity of an antigen but are not necessarily immunogenic themselves.

Immunostimulatory agents or extrinsic adjuvants have been used for many years to improve the host immune responses to immunogenic compositions including vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established and, more recently, a HBsAg vaccine has been adjuvanted with alum. While the usefulness of alum is well established for some applications, it has limitations. For example, it is ineffective for influenza vaccination and inconsistently elicits a cell mediated immune response. The antibodies elicited by alum-adjuvanted antigens are mainly of the IgG1 isotype in the mouse, which may not be optimal for protection by some vaccinal agents.

Furthermore, studies in rats have demonstrated that alum acts as an IgE adjuvant (ref. 1—Throughout this application, various references are referred to in parenthesis to more fully describe the state of the art to which the invention pertains. Full bibliographic information for each citation is found at the end of the specification, immediately preceding the Claims. The disclosure of other references are incorporated by reference into the present disclosures. Studies with tetanus and diphtheria toxoid vaccines also indicate that alum adsorption of vaccines induces IgE antibodies in humans (refs. 2, 3, 4). Therefore, although the inclusion of an aluminum salt in a vaccine formulation may improve its immunogenicity and potency, the fact that it can induce local granulomas and IgE antibodies which may contribute to hypersensitivity reactions warrants careful examination of the practice of alum-adsorption of vaccines for human and animal use.

Some characteristics of desirable adjuvants include:

(1) a lack of toxicity;

(2) an ability to stimulate a long-lasting immune response;

(3) simplicity of manufacture and stability in long-term storage;

(4) an ability to elicit both cellular and humoral immune responses to antigens administered by various routes, if required;

(5) synergy with other adjuvants;

(6) a capability of selectively interacting with populations of antigen presenting cells (APC);

(7) an ability to elicit appropriate $T_H1$ or $T_H2$ cell-specific immune responses;

(8) an ability to selectively increase appropriate antibody isotype levels (for example, IgA) against antigens; and (9) that they do not contribute to hypersensitivity reactions.

Of relevance to the present invention is a discussion of the development of *pertussis* vaccines presented below.

Thus, *pertussis* or whooping cough is a serious respiratory disease caused by the infection of the respiratory tract by the gram negative organism *Bordetella pertussis. Pertussis* is a major cause of childhood morbidity and is implicated in 360,000 deaths annually (ref. 5). The most effective method of control of the spread of the disease has proven to be the use of widespread immunization programs. The whole cell *pertussis* vaccine which was shown to have clinical efficacy in the 1950's, has been effective in controlling *pertussis* epidemics (refs. 6, 7, 8). The value of the vaccine was illustrated when Japan, Sweden and Great Britain abandoned routine childhood *pertussis* immunization. Shortly thereafter, these countries experienced major epidemics of *pertussis* (refs. 9, 10, 11, 12).

Although the whole cell *pertussis* vaccine is effective in preventing the incidence and spread of disease, the acceptance and uptak of the vaccine has been limited due to reports of vaccine associated adverse effects. Therefore, an impetus for the creation of a non-reactogenic, effective and well defined acellular component *pertussis* vaccine was created. One of the key features of the acellular vaccine is the chemically detoxified *pertussis* toxin (PT) component. The presence of native *pertussis* toxin in the whole cell vaccine has been a source of concern as studies in animal models have shown that it can induce lymphocytosis, histamine sensitization, potentiation of anaphylaxis and IgE antibodies, enhancement of insulin secretion and many other systemic effects (ref. 13). The acellular *pertussis* vaccines differ with respect to the combinations and quantities of *Bordetella pertussis* antigens included in the vaccines but the key antigens include the agglutinogens, pertactin, filamentous hemagglutinin (FHA) and *pertussis* toxin (PT). Although the acellular vaccine has been demonstrated to be immunogenic and of comparable efficacy to the whole cell vaccine, it has not been as effective in preventing bacterial colonization (ref. 14). In addition, the results from a Swedish field trial comparing acellular and whole cell *pertussis* vaccines indicated that the formaldehyde inactivated *pertussis* toxin present in the acellular vaccines showed evidence of reversion to toxicity (ref. 15). Therefore, other methods of inactivating the *pertussis* toxin molecule were required.

To overcome the drawbacks of chemical detoxification, several groups developed genetically detoxified *pertussis* mutant holotoxin molecules (refs. 16, 17, 18, 19, 20, 21). A promising candidate was the K9G129 mutant. Not only was the immunogenicity of the molecule retained, but the toxicity of this recombinant toxin was greatly diminished (refs. 18, 19, 21). In addition, immunization with the K9G129 mutant stimulated both humoral and cellular *pertussis* antigen specific responses (ref. 22). Although many clinical trials base the evaluation of the immunogenicity of a vaccine solely on the antibody response following immunization, studies indicate an important role for cellular immunity in protection against this disease. In animal models, the cellular immune response has been demonstrated to be important in the protective response against *pertussis* as the adoptive transfer of cells from convalescent animals into sublethally irradiated animals conferred protection from challenge with *Bordetella pertussis* organisms while the passive transfer of immune serum did not (refs. 23, 24). A retrospective study in humans indicated that cell mediated immunity to *Bordetella pertussis* correlated with a positive history of *pertussis* (ref. 25). Following natural *pertussis* infection in humans, both an antibody and cellular immune response are observed (ref. 26). However, immunization with either the whole cell or acellular component vaccines resulted in variable *pertussis* antigen-specific cellular immune responses (refs. 27, 28). It appeared that the chemical detoxification of the *pertussis* toxin component destroyed its T cell immunogenicity while the antibody responses were unaffected (ref. 26). Therefore, only the genetically detoxified *pertussis* toxin molecule could be used to stimulate both a cellular and humoral immune response.

The use of the recombinant PT mutant, K9G129, as a *pertussis* vaccine component has been well described. A number of different forms of the vaccine have been suggested. Two formulations have been evaluated in humans. The first formulation consisted of 15 μg of the PT mutant which was alum-adsorbed with a total of 0.5 mg of alum per dose (refs. 22, 29) while the other formulation contained 7.5 μg of the K9G129 mutant as well as 10 μg FHA and 10 μg pertactin and was also alum adsorbed (ref. 30). These studies indicated that the genetically detoxified *pertussis* vaccine candidate was not only safe, immunogenic and could induce a cell mediated response, but, when combined with the FHA and pertactin antigens, it also provided better protection in the intracerebral challenge test than a chemically detoxified component *pertussis* vaccine (ref. 30). Other suggested formulations include a formaldehyde-treated K9G129 component (ref. 31) and a cellular vaccine derived from a strain of *Bordetella pertussis* producing the genetically inactivated K9G129 *pertussis* toxin molecule (ref. 32). The formaldehyde treatment of the K9G129 molecule altered the immunogenicity of the molecule as lower amounts of specific antibodies were induced. The protective ability of the molecule was also decreased as it was less effective in the intracerebral challenge assay (ref. 32). However, the recombinant cellular vaccine derived from the K9G129 producing strain proved to be as effective as the whole cell *pertussis* vaccine (ref. 32).

Although the preceeding formulations demonstrate the advantages of improved safety and efficacy associated with the use of a genetically detoxified *pertussis* toxin molecule, they do not address the adverse effects of DPT (diphtheria, *pertussis* and tetanus) vaccination not associated with the *pertussis* molecule component (refs. 33, 46). All of the stated formulations involved the use of either 0.3 mg of aluminum phosphate (ref. 32) or 0.5 mg aluminum hydroxide (refs. 29, 30). Aluminum salts were introduced into the DT and DPT vaccine formulations as an adjuvant that would potentiate strong antibody responses when the levels of the toxoids or the numbers of *Bordetella pertussis* organisms were decreased to avoid adverse reactions (refs. 34, 35) and alum is now routinely used in these vaccines as an adjuvant. However, years of field experience with these adsorbed *pertussis* vaccines and studies (refs. 36, 37) have demonstrated that, although they contained less of the identified reactogenic vaccine components, local reactions were nonetheless precipitated (refs. 38, 39, 40, 41, 42). Histopathological examination of local abscesses produced following vaccination revealed aluminum hydroxide inclusions in giant cells (ref. 38). Investigation into the frequency of such granulomas indicated that they were associated with the aluminum content in the vaccine as placebo immunized groups which received only the aluminum fraction of the vaccine, exhibited abscess formation at a similar reaction rate (ref. 43). Further evidence in support of the role of aluminum in these local reactions was derived from studies comparing aluminum adjuvant adsorbed and plain cholera and tetanus vaccines (refs. 44, 45). Deep innoculation of the vaccine into the muscle decreases the incidence of these abscesses but although improved techniques can prevent the formation of abscesses (ref. 39), the potentiation of IgE responses by aluminum salts is not affected.

It would be advantageous to provide immunogenic compositions having modulated immune responses to the constituent antigens without the disadvantages of local toxicity and contribution to hypersensitivity of prior art extrinsic adjuvants.

SUMMARY OF INVENTION

The present invention relates to avoiding the problems associated with the use of alum as an adjuvant in immunogenic compositions by employing a genetically-detoxified *pertussis* holotoxin, which itself may be immunogenic, to effect modulation of an immune response to a non-*Bordetella* antigen.

While the elimination of alum from vaccine formulations could have been an approach to address to the problems associated therewith, as noted above, alum was included in vaccine formulations to provide an enhanced immune response to the antigens in the formulation. Elimination of alum, therefore, would be expected to lead to a less effective formulation and would be unlikely to have been proposed.

However, the genetically-detoxified *pertussis* holotoxin surprisingly provides a modulation of the immune response of a non-*Bordetella* antigen which enables vaccine formulations and other immunogenic compositions to be provided which exhibit immune responses at least equivalent to those achieved by adjuvanting with alum.

Accordingly, in one aspect of the present invention, there is provided an immunogenic composition, which comprises a genetically-detoxified *pertussis* holotoxin, and at least one other, non-*Bordetella*, antigen, wherein said genetically-detoxified *pertussis* holotoxin is present in an amount sufficient to modulate an immune response to said other antigen in the absence of an extrinsic adjuvant.

The immune response which is modulated by the presence of the genetically-detoxified *pertussis* holotoxin may be humoral and/or a cellular immune response. In particular, the modulated immune response may be an enhanced IgG and/or cellular response to the other antigen.

The at least one other, non-*Bordetella* antigen present in the immunogenic composition may provide a protective immune response to at least one pathogen, which may be a bacterial, viral or parasitic pathogen. The antigen may be selected from a wide range of pathogens. Representative pathogens include *Corynebacterium diphtheriae, Clostridium tetani, paramyxoviridae, haemophilus*, influenza, hepatitis, meningococci, streptococci, *schistosoma* and trypanosome. The antigen also may be selected from cancer-associated antigens, particularly melanoma, bladder, lung, cervical and prostate cancer antigens.

The at least one other non-*Bordetella* antigen may comprise inactivated tumor cells or membrane fractions thereof. Tumor cells may be removed from a cancerous host and then inactivated in any convenient manner, for example, by irradiation or chemical inactivation. The inactivated cells and/or membrane fraction thereof then are mixed with the genetically-detoxified holotoxin to provide an immunogenic composition according to the invention. Such composition then may be administered to a naive (i.e. non-cancer burdened) host to confer prophylactic protection against tumor development. In addition, such composition may be administered to a tumor-burdened host to promote an anti-tumor immune response in the host.

The genetically-detoxified *pertussis* holotoxin may itself be immunoprotective but the immunomodulating effect thereof may be obtained in the absence of an immune response to the holotoxin. The provision of genetically-detoxified *pertussis* holotoxins is described in U.S. Pat. Nos. 5,085,862 and 5,221,618, assigned to the assignee hereof and the disclosures of which are incorporated herein by reference.

The term "genetically-detoxified" as used herein has the same meaning as in the aforementioned U.S. Pat. Nos. 5,085,862 and 5,221,618, namely a *pertussis* holotoxin mutant which exhibits a residual toxicity of about 1% or less, preferably less than about 0.5% of that of the native toxin. The residual toxicity is determined by CHO cell clustering assay and ADP-ribosyl-transferase activity.

Such genetically-detoxified *pertussis* holotoxin may be formed by mutagenesis of a nucleotide sequence coding for the holotoxin, as described in the above-mentioned patents, so that at least one amino acid is removed or replaced. Multiple amino acids also may be removed or replaced.

The at least one amino acid which is removed or replaced may be present in the S1 subunit, specifically $ARG^9$, $ARG^{13}$, $TRP^{26}$, $ARG^{58}$ and $GLU^{129}$. Where multiple amino acids are removed or replaced, it is preferred to remove or replace (S1)$ARG^9GLU^{129}$. When such mutation is effected, it is preferred to replace $ARG^9$ by $CYS^9$ and $GLU^{129}$ by $GLY^{129}$. (This specific mutant is sometimes depicted herein as K9G129.)

Below are Tables 1a and 2 containing details of several mutations of *pertussis* holotoxin which may be used as the genetically-detoxified *pertussis* holotoxin in the immunogenic compositions provided herein. (The Tables appear at the end of the descriptive text). Table 1b contains details of the in vivo characterization of the mutations of Table 1a.

The immunogenic compositions of the invention may contain at least one additional *Bordetella* antigen, including agglutinogens, FHA and pertactin.

The immunogenic compositions provided herein may be formulated in the substantial absence of an extrinsic adjuvant as a vaccine for human or animal administration. Such vaccine composition may exhibit a decreased IgE response.

In one embodiment of the invention, the immunogenic compositions of the invention may be formulated in the substantial absence of alum as a multivalent vaccine comprising the genetically-detoxified *pertussis* holotoxin in an immunoprotective form and amount along with diphtheria toxoid and tetanus toxoid as the other antigens, thereby providing a DTP vaccine formulation from which alum or other extrinsic adjuvant is absent. Such DTP vaccine formulations usually also contain other *Bordetella* antigens, including agglutinogens, FHA and pertactin.

In another aspect, the present invention provides a method of obtaining a modulated immune response to an antigen in a host, including a human, which comprises administering at least one non-*Bordetella* antigen to the host, and coadministering to the host a genetically-detoxified *pertussis* holotoxin in an amount sufficient to modulate an immune response to the other antigen in the absence of an extrinsic adjuvant.

As noted above, the immune response may be a humoral and/or a cellular immune response and the modulated immune response may be an enhanced IgG and/or cellular immune response. The administration of the *pertussis* holotoxin and other antigen may be effected by administering to the host a composition as described above and provided according to the invention.

In a particular embodiment of the present invention antigens and adjuvants are coadministered. In this application the term "coadministration" means simultaneous administrations or administrations within a short time period such as between several minutes or hours and up to 3 days. The coadministrations may be at the same or different sites and by the same or different routes.

BRIEF DESCRIPTION OF THE FIGURES

The present invention will be further understood from the following description with reference to the Figures in which.

GENERAL DESCRIPTION OF INVENTION

Figure 1:
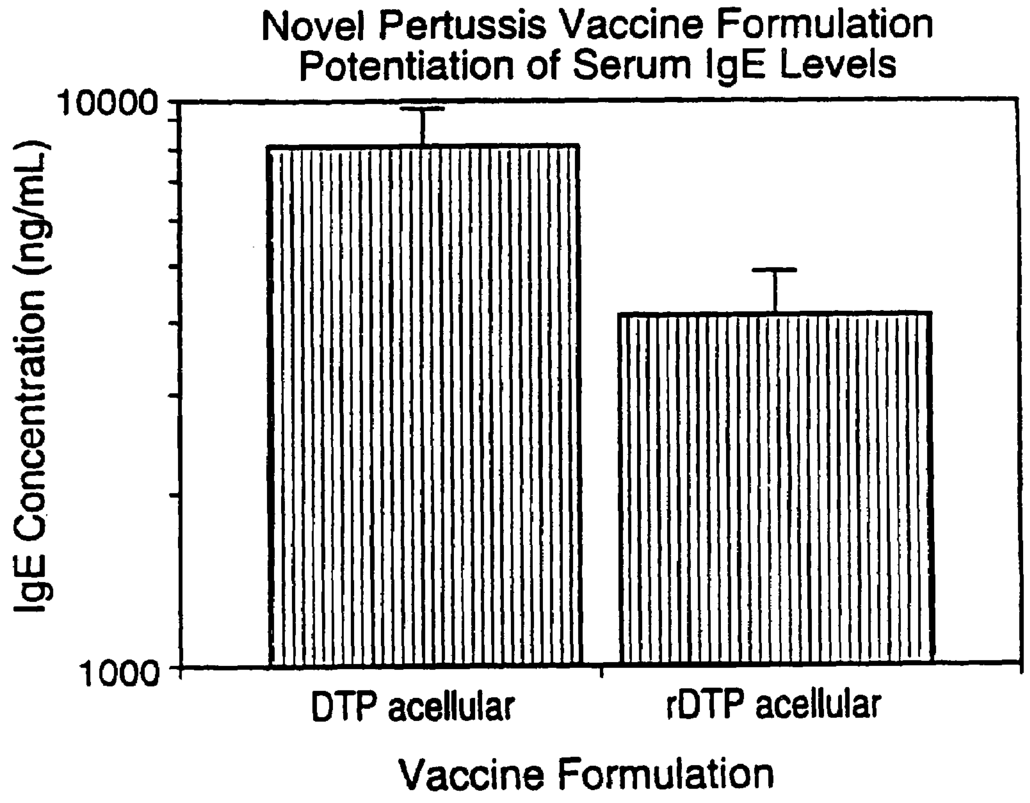
FIG. 1 shows the potentiation of murine serum IgE antibody production by immunogenic compositions of the present invention.

Referring to FIG. 1, there is illustrated the potentiation of serum IgE levels in mice immunized with a chemically inactivated acellular alum-adjuvanted DTP vaccine and a non-alum adjuvanted rDTP acellular vaccine comprising the genetically-detoxified K9G129 PT analog. The results indicate that the serum IgE levels in mice immunized with the rDTP acellular vaccine were significantly decreased ($p<0.05$) relative to the DTP acellular vaccine containing the chemically toxoided *pertussis* toxin molecule.

Figure 2:
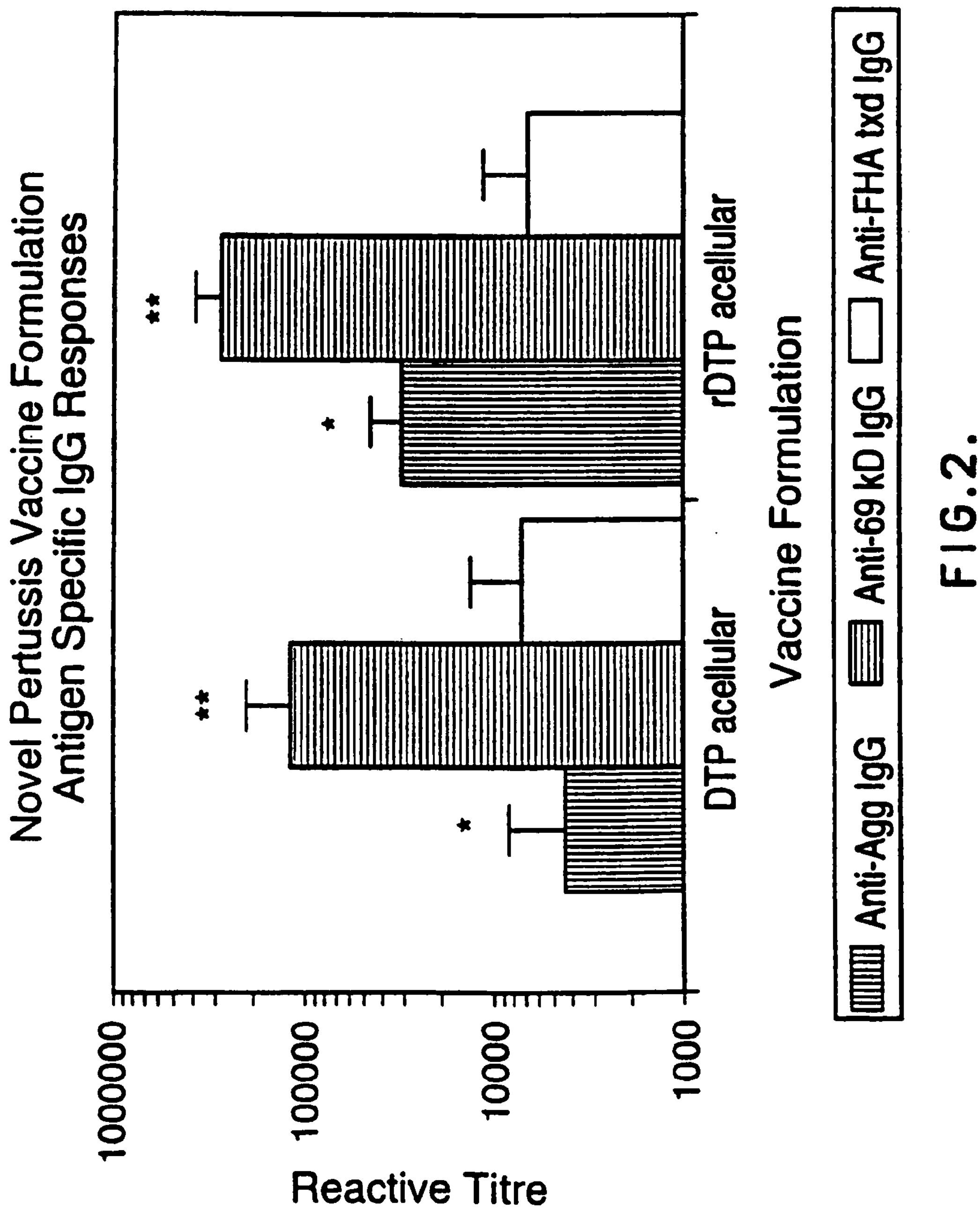
FIG. 2 shows the production of IgG antibodies by immunogenic compositions of the present invention.
Figure 3:
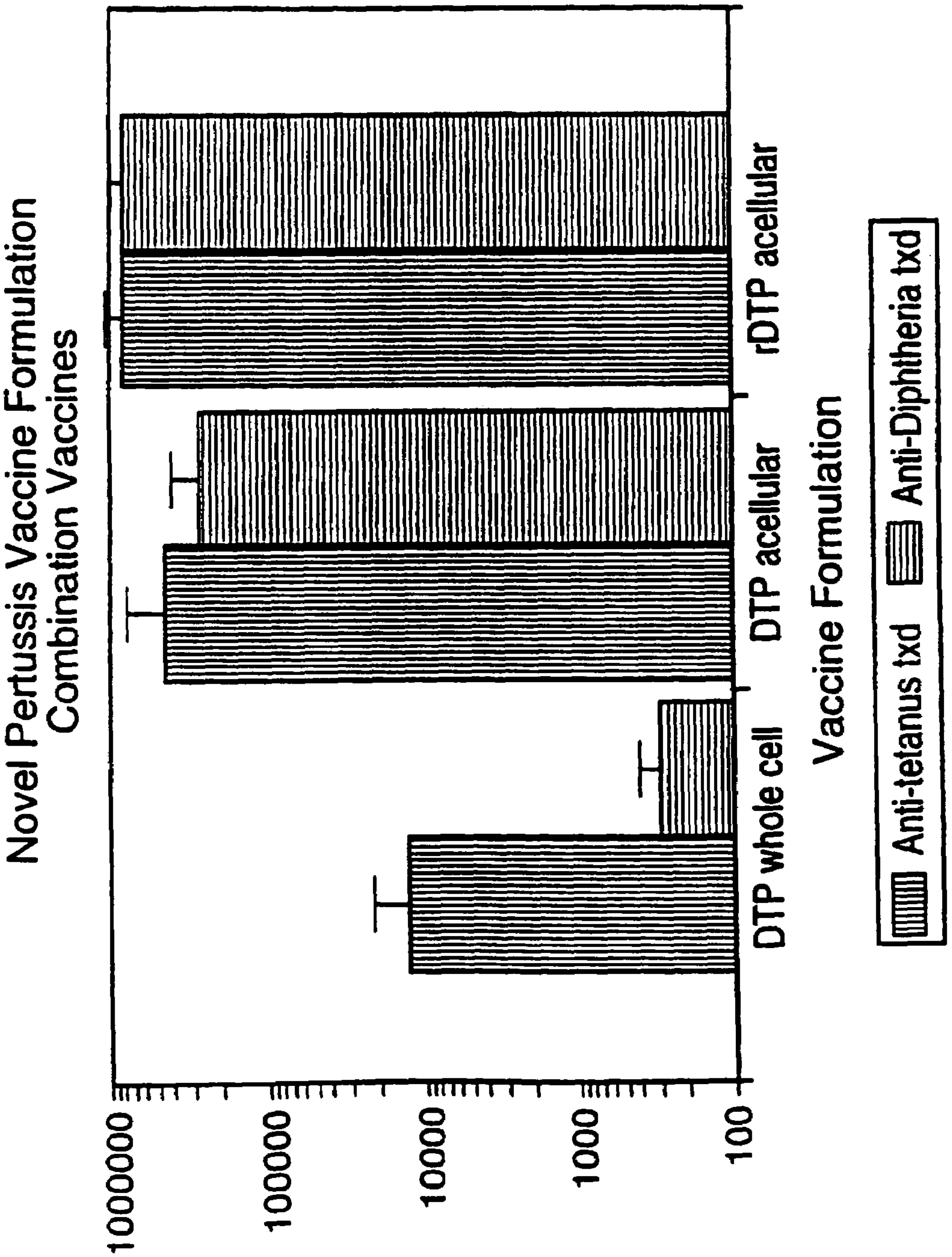
FIG. 3 shows the production of IgG antibodies by multivalent vaccines of the present invention.

Referring to FIGS. 2 and 3 and Table 3, there is illustrated a comparison of antigen specific antibody levels produced following immunization of mice with an alum adjuvanted DTP whole cell vaccine, an alum-adjuvanted DTP acellular vaccine preparation and a DTP vaccine containing the genetically-detoxified PT analog K9G129 not adjuvanted with alum. The results shown in Table 3 indicate that the anti-PT IgG response and the CHO neutralization titres produced by the alum-adjuvanted DTP acellular vaccine and the non-alum-adjuvanted recombinant DTP acellular vaccine are equivalent. Thus, although the alum-free recombinant formulation demonstrated decreased IgE potentiating activity, it nonetheless retained its effectiveness as a *pertussis* vaccine as indicated by these anti-*pertussis* toxin IgG titres. Further evidence of the retention of PT-specific immunogenicity was obtained from CHO cell neutralization assays. Significantly, higher levels of anti-agglutinogen 2+3 and anti-69 kD (pertactin) IgG antibodies were detected in the serum samples from mice immunized with alum-free recombinant formulation ($p<0.05$). The anti-FHA toxoid IgG responses were equivalent in sera obtained from mice immunized with either of the vaccines.

FIG. 3 shows the anti-tetanus toxoid and anti-diphtheria toxoid IgG antibody levels in sera of mice immunized with either the whole cell *pertussis* vaccine, the defined component acellular DTP vaccine containing the glutaraldehyde-detoxified *pertussis* molecule or the alum-free recombinant acellular DTP vaccine. The diphtheria and tetanus toxoid components in the latter vaccine were also devoid of alum. The results indicate that the acellular formulations induce significantly higher anti-tetanus toxoid and particularly anti-diphtheria toxoid IgG antibodies as measured by this assay. Furthermore, the alum-free recombinant formulation induced significantly higher anti-tetanus and diphtheria toxoid IgG responses relative to the acellular component DTP vaccine.

Figure 4:
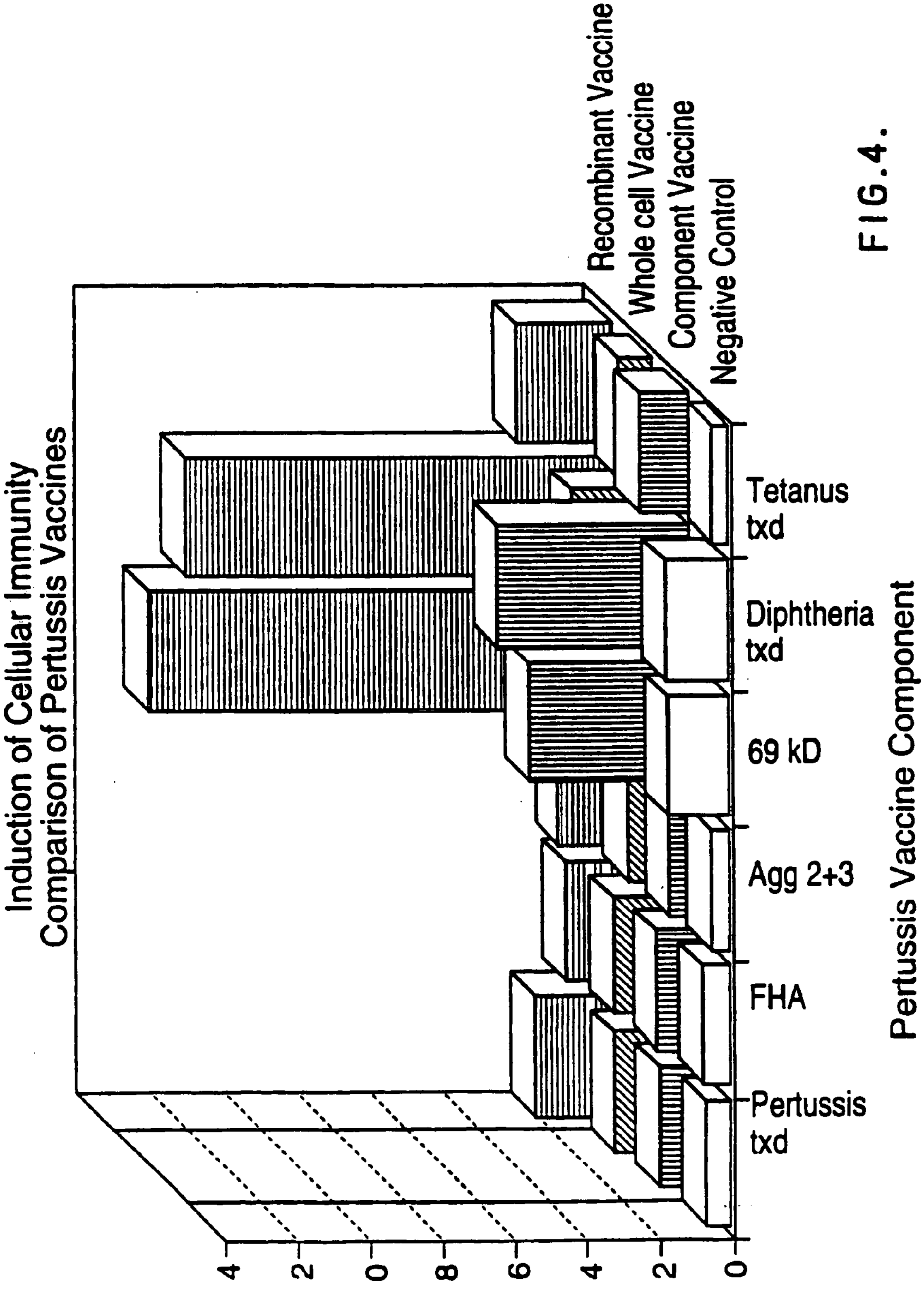
FIG. 4 shows the induction of cellular immune responses by multivalent vaccines of the present invention.

The ability of the DTP vaccine formulations to induce antigen-specific cellular immune responses was evaluated in vitro and the results are shown in FIG. 4. Splenocytes derived from mice immunized with either the whole cell, acellular or alum-free recombinant acellular DTP vaccines were cultured in the presence of the specific vaccine antigens. The whole cell DTP vaccine induced a significant anti-diphtheria toxoid cellular response although not to the same degree as that generated by the acellular component DTP vaccine. The acellular component vaccine induced a relatively poor *pertussis* antigen specific proliferative response with the exception of the anti-69 kD and anti-diphtheria toxoid responses. Of significance, however, was the markedly increased antigen-specific proliferative index induced by the alum-free recombinant acellular formulation in response to all the antigens tested. The recombinant formulation clearly induced the highest levels of antigen-specific proliferative responses of any of the vaccines tested.

In accordance with an embodiment of the invention there is provided (as an example of an immunogenic composition comprising a genetically-detoxified *pertussis* holotoxin and at least one other non-*Bordetella* antigen wherein said genetically-detoxified *pertussis* holotoxin is present in an amount sufficient to modulated an immune response to said other antigen in the absence of an extrinsic adjuvant) an alum-free acellular DPT vaccine containing the genetically-detoxified PT analog K9G129. Thus, although the alum-free formulation does not contain an extrinsic (e.g. a mineral) adjuvant it does contain an adjuvant nonetheless as the K9G129 mutant acts not only as an antigen but as an adjuvant (i.e. a proteinaceous adjuvant) as well. This property is apparent in the *pertussis* antigen specific responses measured by enzyme immunoassay (FIG. 2). Significantly higher anti-agglutinogen 2+3 and anti-69 kD (pertactin) IgG responses were evident in the serum samples derived from mice immunized with the alum-free recombinant acellular *pertussis* vaccine formulation while the FHA toxoid specific responses were equivalent. Therefore, the new formulation induced antibody responses specific for *pertussis* vaccine antigens at levels that were either comparable or greater than the levels induced by the alum-adsorbed acellular *pertussis* vaccine.

The general intrinsic adjuvant activity of the K9G129 mutant for other vaccine antigens (such as those antigens present in human vaccines, such as paediatric combination vaccines) was also evaluated. The tetanus and diphtheria toxoid specific IgG responses in serum obtained from mice immunized with either the alum adsorbed whole cell or acellular *pertussis* vaccines or the alum free recombinant vaccine were compared (FIG. 3). The tetanus and diphtheria specific IgG titres in the serum of mice immunized with the whole cell vaccine were significantly lower than those observed in either of the acellular DTP immunized groups. Although the alum-adsorbed DTP vaccine induced significantly higher toxoid specific responses relative to the whole cell vaccine immunized group, of all the vaccine formulations tested, the alum-free formulation induced the highest titres of toxoid specific IgG. Therefore, the adjuvant activity of the K9G129 mutant is not restricted to only *Bordetella* antigens. The invention extends to a multivalent vaccine containing protective antigens for a plurality of pathogens.

Vaccine Preparation and Use

As indicated above, the present invention in one embodiment provides immunogenic compositions, suitable to be used as, for example, vaccines. The immunogenic composition elicits an immune response by the host to which it is administered including the production of antibodies by the host. The immunogenic compositions include at least one non-*Bordetella* antigen in one embodiment. This antigen may be an inactivated pathogen or an antigenic fraction of a pathogen. The pathogen may be, for example, a virus, a bacterium or a parasite. The pathogen may be inactivated by a chemical agent, such as formaldehyde, glutaraldehyde, β-propiolactone, ethyleneimine and derivatives, or other compounds. The pathogen may also be inactivated by a physical agent, such as UV radiation, gamma radiation, "heat shock" and X-ray radiation. Representive pathogens from which the antigen may be derived include *Corynebacterium diphtheriae, Clostridium tetani, paramyxoviridae, haemophilus*, influenza, hepatitis, meningococci, streptococci, *schistosoma* and trypanosome.

An antigenic fraction of a pathogen can be produced by means of chemical or physical decomposition methods, followed, if desired, by separation of a fraction by means of chromatography, centrifugation and similar techniques. In general, low molecular components are then obtained which, although purified, may have low immunogenicity, alternative antigens include cancer-specific antigens including melanoma, lung, cervical, prostate and bladder cancer antigens. Alternatively, antigens or haptens can be prepared by means of organic synthetic methods, or, in the case of, for example, polypeptides and proteins, by means of recombinant DNA methods.

The immunogenic compositions may be prepared as injectables, as liquid solutions or emulsions. The antigens and immunogenic compositions may be mixed with physiologically acceptable carriers which are compatible therewith. These may include water, saline, dextrose, glycerol, ethanol and combinations thereof. The vaccine may further contain auxiliary substances, such as wetting or emulsifying agents or pH buffering agents, to further enhance their effectiveness. Vaccines may be administered by injection subcutaneously or intramuscularly.

Alternatively, the immunogenic compositions provided by the present invention, may be delivered in a manner to evoke an immune response at mucosal surfaces. Thus, the immunogenic composition may be administered to mucosal surfaces by, for example, the nasal, anal, vaginal or oral (intragastric) routes. Alternatively, other modes of administration including suppositories may be desirable. For suppositories, binders and carriers may include, for example, polyalkylene glycols and triglycerides. Oral formulations may include normally employed incipients, such as pharmaceutical grades of saccharine, cellulose and magnesium carbonate.

These compositions may take the form of solutions, suspensions, tablets, pills, capsules, sustained release formulations or powders and contain 1 to 95% of the immunogenic compositions of the present invention.

The immunogenic compositions are administered in a manner compatible with the dosage formulation, and in such amount as to be therapeutically effective, protective and immunogenic. The quantity to be administered depends on the subject to the immunized, including, for example, the capacity of the subject's immune system to synthesize antibodies, and if needed, to produce a cell-mediated immune response. Precise amounts of antigen and immunogenic composition to be administered depend on the judgement of the practitioner. However, suitable dosage ranges are readily determinable by those skilled in the art and may be of the order of micrograms to milligrams. Suitable regimes for initial administration and booster doses are also variable, but may include an initial administration followed by subsequent administrations. The dosage of the vaccine may also depend on the route of administration and will vary according to the size of the host.

The concentration of antigens in an immunogenic composition according to the invention is in general 1 to 95%. A vaccine which contains antigenic material of only one pathogen is a monovalent vaccine. Vaccines which contain antigenic material of several pathogens are combined vaccines and also belong to the present invention. Such combined or multivalent vaccines contain, for example, material from various pathogens or from various strains of the same pathogen, or from combinations of various pathogens.

Immunoassays

In one embodiment, the immunogenic composition of the present invention are useful for the generation antigen-specific antibodies that are themselves useful in the specific identification of that antigen in an immunoassay. Such immunoassays include enzyme-linked immunosorbent assays (ELISA), RIAs and other non-enzyme linked antibody binding assays or procedures known in the art. In ELISA assays, the antigen-specific antibodies are immobilized onto a selected surface; for example, the wells of a polystyrene microtiter plate. After washing to remove incompletely adsorbed antibodies, a nonspecific protein, such as a solution of bovine serum albumin (BSA) or casein, that is known to be antigenically neutral with regard to the test sample may be bound to the selected surface. This allows for blocking of nonspecific adsorption sites on the immobilizing surface and thus reduces the background caused by nonspecific bindings of antigens onto the surface. The immobilizing surface is then contacted with a sample, such as clinical or biological materials, to be tested in a manner conducive to immune complex (antigen/antibody) formation. This may include diluting the sample with diluents, such as BSA, bovine gamma globulin (BGG) and/or phosphate buffered saline (PBS)/Tween. The sample is then allowed to incubate for from about 2 to 4 hours, at temperatures such as of the order of about 25° to 37° C. Following incubation, the sample-contacted surface is washed to remove non-immunocomplexed material. The washing procedure may include washing with a solution such as PBS/Tween, or a borate buffer.

Following formation of specific immunocomplexes between the antigen in the test sample and the bound antigen-specific antibodies, and subsequent washing, the occurrence, and even amount, of immunocomplex formation may be determined by subjecting the immunocomplex to a second antibody having specificity for the antigen. To provide detecting means, the second antibody may have an associated activity, such as an enzymatic activity, that will generate, for example, a colour development upon incubating with an appropriate chromogenic substrate. Quantification may then achieved by measuring the degree of colour generation using, for example, a visible spectra spectrophotometer.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Example 1

This Example describes the formulation of vaccines.

The DPT whole-cell vaccine and an experimental component acellular vaccine were produced by Connaught Laboratories Ltd. The component acellular *pertussis* vaccine was alum adsorbed (1.5 mg/dose) and consisted of 10 μg protein nitrogen of glutaraldehyde toxoided *pertussis* toxin, 5 μg protein nitrogen each of FHA and agglutinogens 2 and 3 and 3 μg of pertactin along with 5 Lf of tetanus toxoid and 25 Lf of diphtheria toxoid per dose. The recombinant component vaccine also contained 5 μg protein nitrogen each of FHA and agglutinogens 2 and 3 and 3 μg protein nitrogen of pertactin in addition to 5 Lf of tetanus toxoid and 25 Lf of diphtheria toxoid per dose. However, it varied from the other acellular vaccine in that it contained 20 μg protein nitrogen of the recombinant PT mutant holotoxin, K9G129, and was not alum adsorbed. The K9G129 *pertussis* toxin molecule as well as the purified FHA, agg 2+3 and pertactin components were obtained individually from Connaught Laboratories Ltd.

Example 2

This Example describes immunization of animals.

Female BALB/c mice weighing 15 to 18 grams were obtained from Charles River Canada (St. Constant, Quebec). The mice were housed in microisolators and used in accordance with the guidelines set by the Canadian Council on Animal Care (CCAC). The animals were specific pathogen free and the housing rooms were monitored for Murine Hepatitis Virus outbreaks through the use of sentinel mice. Water was provided ad libitum and the diet was ovalbumin-free. The mice were immunized on Day 0 with the vaccine formulations in groups of six. A booster dose of vaccine was administered on Day 21. On Day 28 the animals were bled via jugular vein laceration and splenectomized. The serum samples were stored at −20° C. until assayed.

Example 3

This Example describes antigen specific immunoassays.

The vaccine antigen specific IgG responses were determined by indirect EIA. The antigens of interest were *pertussis* toxin, pertactin, filamentous hemagglutinin, agglutinogens, as well as diphtheria and tetanus toxoids. High binding capacity microplates (Nunc) were coated with 4 μg/mL of each of the above antigens in a volume of 50 uls/well of 50 mM carbonate buffer pH 9.6. After an overnight incubation, the plates were washed and successively blocked with a 0.1% solution of bovine serum albumin (Sigma) for one hour at room temperature. The excess block was removed and the microplates were washed. The murine serum samples were then serially diluted in PBS-Tween 20 (0.05%) and plated out at a volume of 100 uls. The samples were incubated overnight at 4° C. The antigen specific fraction of IgG antibodies was detected by a peroxidase conjugated sheep anti-mouse IgG conjugate (Jackson Laboratories). The plates were developed with the TMB substrate as above and were read at dual wavelengths of 450 nm and 540 nm in the Multiskan MCC 340 MkII microplate reader. Reactive titres were defined as the dilution at which the absorbance of the test sample was equivalent to the mean plus three standard deviations of the negative control absorbance values. The geometric means and 95% confidence intervals were calculated and the groups were compared using the Student's t-test.

Example 4

This Example describes the determination of ovalbumin specific IgG subclass profiles.

Example 5

This Example describes total IgE immunoassays.

The serum total IgE levels were assessed by indirect EIA. Nunc immunoplates (Gibco/BRL) were coated at room temperature overnight with a sheep anti-mouse IgE polyclonal antiserum (Serotec) diluted in 50 mM carbonate buffer pH 9.6. The next day the plates were washed in PBS containing 0.05% Tween 20 (J. T. Baker) and then blocked with 0.1% casein amino acids (Difco) for one hour at room temperture. After the excess blocking solution was washed off the plates, the murine serum samples were serially diluted three-fold in the assay diluent and plates out onto the microplate at 100 uls per well. The samples were incubated overnight at 4° C. To detect the bound IgE antibodies, a biotinylated rat anti-mouse Ige monoclonal antibody (Serotec) was added to each well at a concentration of 2 ug/mL and incubated for one hour at room temperature. After washing, peroxidase conjugated streptavidin (Dimension Laboratories) was added to each well. The amount of IgE bound to the wells was assessed by adding the enzyme substrate, 10% tetramethylbenzidine (TMB) (ADI Diagnostics) in 0.005% hydrogen peroxide water (Fisher Scientific). The reaction was stopped after ten minutes with 1M sulfuric acid (Fisher Scientific). The absorbance of the wells was measured at 450 nm with a background correction at 540 nm on a Multiskan MCC 340 MkII microplate reader (Flow Laboratories). The serum IgE levels were quantitated by calibrating the sample absorbances against a standard curve generated by a serially diluted IgE murine myeloma protein run on each plate. The geometric means and 95% confidence intervals were calculated for each treatment group and the groups were compared using the Student's t-test and $p<0.05$.

Example 6

This Example describes the determination of ovalbumin specific IgGF immunoglobulins.

The levels of IL-4 and IFN-γ were determined in a sandwich EIA. Briefly, 96 well Nunc Maxisorp microplates (Gibco/BRL) were coated overnight at room temperature with cytokine monospecific rat monoclonal antibodies. These antibodies were obtained from Pharmingen and derived from the following respective clones: IL-4, clone 11B11; IL-5; IFN-γ, clone R4-6A2. The monoclonal antibodies were diluted to a concentration of 2 μg/mL in 50 mM carbonate buffer pH 9.6. The following day, the plates were washed in PBS-Tween 20 0.05% (PBS-T) and nonspecific binding sites were blocked by the addition of a 1% bovine serum albumin (Sigma) solution diluted in PBS-T. Following incubation for one hour at room temperature, the excess block was washed from the plates and undiluted culture supernatants were added to the wells in duplicate. The appropriate recombinant standards for each cytokine (recombinant IL-4 obtained from Pharmingen, recombinant IFN-γ purchased from Genzyme) were diluted to the appropriate concentrations (initial concentration of 100 ng/mL or 1000 ng/mL for IL-10 EIA) and serially diluted three-fold in RPM 1640 (Sigma) containing 10% fetal bovine serum (FBS). The standards were plated out at 100 μls/well and the microplates were incubated overnight at 4° C. After a vigorous wash in PBS-T, the bound cytokines were detected using a biotinylated monoclonal antibody specific to each cytokine and diluted to a concentration of 2 μg/mL in PBS-T. The antibodies were obtained from Pharmingen and were derived from the following clones: IL-4 clone BVD6-24G2; IFN-γ, clone XMG1.2. After a one hour incubation step at room temperature, a peroxidase conjugated streptavidin preparation (Vector Laboratories) diluted to a concentration of 500 ng/mL was added. A final wash was performed following a one hour incubation at room temperature of the streptavidin preparation. The plates were developed by the addition of the substrate, 10% TMB in 0.05% hydrogen peroxide (Fisher Scientific) water. The reactions were allowed to proceed until suitable colour intensity was reached and were stopped by the addition of 100 μls/well of a 1M solution of sulfuric acid (Fisher Scientific). The absorbances of the reaction wells were read at dual wavelengths (450 nm and 540 nm) on a Multiskan MCC 340 MkII (Flow Laboratories) microplate reader.

The cytokine concentrations in the supernatants were quantitated by calibrating the sample absorbances against the absorbances of the standards of known concentrations using the logistic curvefit algorithm to fit the curve with a minimum correlation coefficient of 99.9%. The ELISA+ software package (Meddata) was used to quantitate the amounts of cytokines present in the supernatants based on the standard curves generated on each plate.

Ovalbumin-specific IgE titres in the sera of immunized mice were determined by use of an indirect antigen capture EIA. Briefly, Nunc Maxisorp microplates (Gibco/BRL) were coated with a rabbit anti-ovalbumin IgG fraction (Cappel Laboratories). The plates were incubated overnight at room temperature. The next day, after washing in PBS-T, the plates were blocked with a solution of 0.1% skimmed milk powder diluted in PBS-T for one hour at room temperature. Next, a solution of ovalbumin diluted to 10 μg/mL in 50 mM carbonate buffer pH 9.6 was added to each well in 100 μl volumes. Following a one hour incubation at room temperature, the ovalbumin solution was washed off the plates. The murine serum samples were then serially diluted three-fold in PBS-T at an initial dilution of 1:40 and a final dilution of 1:87480. 100 ml samples were added per well and incubated overnight at 4° C. After washing the next day, the ovalbumin specific IgE antibodies bound to the plates were detected using a biotinylated rat anti-mouse IgE monoclonal antibody (Clone LO-ME-2, Serotec) diluted to 2 μg/mL in PBS-T. Following a further one hour incubation at room temperature, this antibody was washed off and peroxidase conjugated streptavidin (Vector Laboratories) was added to each well at a concentration of 500 ng/mL. The amount of ovalbumin-specific IgE in the murine serum samples was detected by adding the peroxidase substrate, 10% tetramethylbenzidine (TMB) (ADI Diagnostics) in 0.005% hydrogen peroxide. The color in the wells was allowed to develop for fifteen minutes and the reactions were stopped by the addition of 100 μls of 1M sulfuric acid (Fisher Scientific). The absorbance of the wells was measured in a microplate reader (Multiskan MCC 340 Mk11, Flow Laboratories) at 450 nm with a reading at 540 nm for background correction. Reactive titres were defined as the last dilution at which the absorbance value of the test sample was equivalent to the mean of the absorbance values derived from a negative serum control plus three standard deviations. The geometric means were calculated on log transformed data and expressed with 95% confidence intervals.

Example 7

This Example describes the determination of murine cytokine profiles.

The ovalbumin-specific IgG, IgG1 and IgG2a titres in murine serum samples were measured by indirect EIA. In the IgG2a assay, Nuno Maxisorp 96-well microplates (Gibco/BRL) were coated with a rabbit anti-ovalbumin polyclonal antibody IgG fraction (Cappell Laboratores) diluted in 50 mM carbonate buffer pH 9.6 and incubated overnight at room temperature. Ovalbumin-specific IgG and IgG1 responses were measured on microplates coated directly with ovalbumin (Sigma) diluted to a concentration of 10 μg/mL in 50 mM carbonate buffer. The following day, the microplates were washed in PBS-T and blocked for one hour at room temperature with a solution of 0.1% skimmed milk powder diluted in PBS-T. After a further washing step, a 10 μg/mL solution of ovalbumin (Sigma) diluted in 50 mM carbonate buffer pH 9.6 was added to the IgG2a specific assay. This antigen coat was incubated for one hour at room temperature and was followed by a washing step.

The next step in the assay required the addition of the murine serum samples. In the IgG2a assay, the serum samples were serially diluted three-fold beginning at an initial dilution of 1:40 and ending at a dilution of 1:87480. The IgG and IgG1 assays were carried out with serum samples diluted three-fold starting at an initial dilution of 1:360 and ending at a final dilution of 1:787320. The serum samples were diluted in PBS-T and added to the wells of the microplates in 100 μl volumes. The plates were incubated overnight at 4° C. The next day, the plates were washed and the ovalbumin-specific IgG subclasses of antibodies were detected with biotinylated rat anti-mouse IgG conjugates specific for each IgG antibody subclass (IgG2a conjugate, derived from clone R19-15 and obtained from Pharmingen, IgG1 conjugate, derived from clone LO-MGI-2 and obtained from Serotec) while the IgG responses were detected with a 1:50,000 dilution of a peroxidase-labelled sheep anti-mouse IgG (Fcγ specific, Jackson Laboratories). The conjugated monoclonal antibodies were diluted to a concentration of 2 μg/mL and incubated for one hour at room temperature. After washing, peroxidase conjugated streptavidin was added to each well of the plates containing a biotinylated conjugate at a concentration of 500 ng/mL. The plates were incubated for one hour at room temperature. The bound antigen-specific IgG and IgG subclass antibodies were detected by the addition of the peroxidase substrate, 10% TMB (ADI Diagnostics) diluted in 0.005% hydrogen-peroxide (Fisher Scientific). The reactions were allowed to proceed for a period of ten minutes at which point they were terminated by the addition of 1M sulfuric acid (Fisher Scientific) to each well. The microplates were read on a microplate reader (Multiskan MCC 340 MkII, Flow Laboratories) at dual wavelengths of 450 nm and 540 nm. Reactive titres were defined as the last dilution at which the absorbance of the test sample was equivalent to the mean plus three standard deviations of the negative control absorbance values. The geometric means were calculated on log transformed data and expressed with 95% confidence intervals.

Example 8

This Example describes antigen-specific cellular immune responses.

Murine splenocytes were obtained from the vaccine immunized BALB/c mice on Day 28. The spleens were dissociated into a single cell suspension and washed three times in RPMI 1640 media (Sigma). A cell count was performed using the trypan blue exclusion method and the cells were adjusted to a concentration of $2\times10^6$ cells/mL. The antigens (*pertussis* toxoid, pertactin, FHA, agglutinogens, and non alum-adsorbed diphtheria and tetanus toxoids were diluted to a concentration of 5 μg/mL in RPMI 1640 media containing 10% fetal bovine serum. The antigens were then serially diluted two fold to a concentration of 78 ng/mL. The cells were then added to each well at a final concentration of $1\times10^5$ cells/well. The cultures were left to incubate at 37° C. in a 5% $CO_2$ incubator for 72 hours. At the end of this period, the cells were pulsed with 0.5 μCi/well of tritiated thymidine (Amersham) diluted in sterile PBS (Sigma). After a further 18 hour incubation, the cells were harvested onto glass fibre filter paper using a 96 well harvester (Canberra Packard) and the radioactive counts were read on a Matrix 96 beta counter (Canberra Packard. The results were expressed as stimulation indices which were calculated by dividing the means of the test counts by the means of the background counts on the plate. Each sample was assayed in triplicate.

Example 9

This Example describes the ability of antibodies to neutralize *pertussis* toxin in the CHO cell neutralization assay.

The ability of the antibodies induced by the *pertussis* vaccines to neutralize *pertussis* toxin was assessed in the CHO cell assay as described by Granstrom et al. (ref. 47). The last dilution of antibody at which no significant morphological effects could be seen was defined as the neutralizing titer. The results were expressed as reciprocal neutralizing titers.

Example 10

This example illustrates the use of genetically-detoxified *pertussis* holotoxin to confer prophylactic protection against tumor development.

Thus, the B16 mouse melanoma model (Ref. 54) was used to assess the effectiveness of K9G129 as an adjuvant in cancer immunotherapy. When C57Bl/6 mice were injected subcutaneously with live syngeneic B16-F1 strain of B16 melanoma cells, tumors appeared after about ten days and progressively grew in an exponential manner. Tumor appearance was directly proportional to the dose of cells injected, eg. tumors formed earlier when mice were injected with $10^6$ cells than with $10^4$ cells. Tumors could be delayed by immunizing the mice with B16 melanoma cells that had first been irradiated with 10,000 rads. This delay was also dose dependent. Immunizing with $10^6$ irradiated cells caused a greater delay in tumor appearance than immunizing with $10^5$ irradiated cells, when the mice were subsequently challenged with $10^5$ live cells. Immunizing with $10^4$ irradiated cells caused no significant delay in tumor growth.

The effectiveness of K9G129 as an adjuvant was tested by measuring its ability to delay tumor growth when combined with $10^4$ irradiated cells in an immunization experiment. Six groups of mice with five mice per group were immunized with:

1) cell culture medium (control)

2) $10^4$ irradiated cells

3) $10^4$ irradiated cells+1 μg K9G129

4) $10^4$ irradiated cells+5 μg K9G129

5) $10^4$ irradiated cells+10 μg K9G129

6) $10^4$ irradiated cells+CFA (complete Freunds adjuvant)

The mice were boosted in the same manner two weeks later and then two weeks after the boost they were challenged with $10^5$ live B16 melanoma cells. The appearance of tumors was monitored and the size of growing tumors was measured with calipers, noting both the length and width. The volume of the tumors was calculated by applying these measurements to the formula for an ellipsoid.

Figure 7:
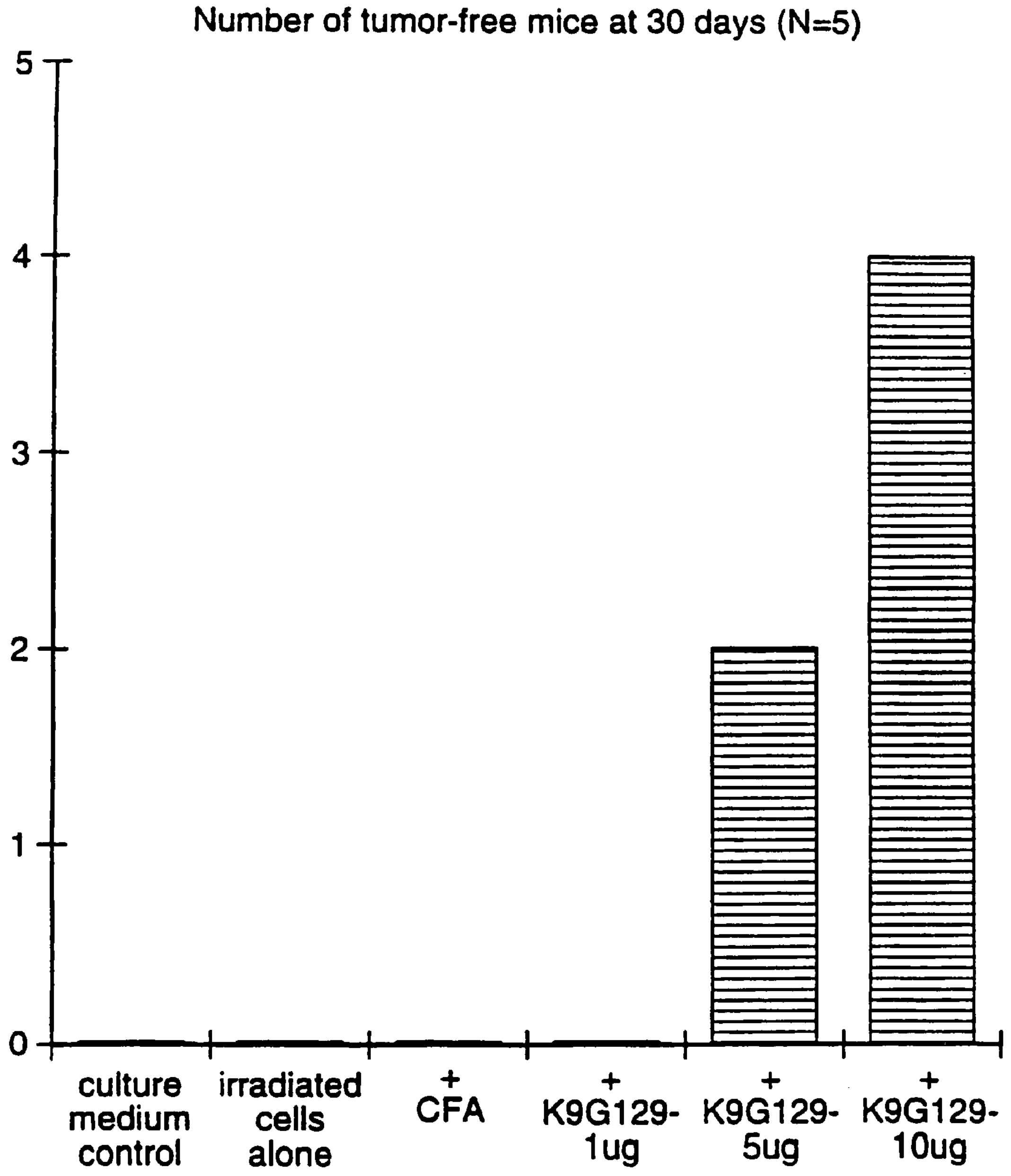
FIG. 7 shows the number of tumor-free mice in immunotherapy experiments conducted herein. Six groups of mice with five mice per group were immunized with cell culture medium as a control and $10^4$ live melanoma cells. The graph shows the number of mice that had no tumor thirty days after the challenge.

K9G129 was effective in a dose dependent manner in delaying the onset of tumor growth. Thirty days after the challenge with $10^5$ live melanoma cells, there were no mice without tumors in the groups that received no immunization (group 1), irradiated cells alone (group 2), or irradiated cells with CFA (group 6). There were also no tumor-free mice in the group that had received irradiated cells with 1 μg of K9G129 (group 3). However there were two and four mice respectively that had no tumor from the groups that had received irradiated cells with 5 μg and 10 μg of K9G129 (groups 4 and 5) (FIG. 7). These results show a large delay in tumor appearance mediated by the two higher concentrations of K9G129.

Figure 8:
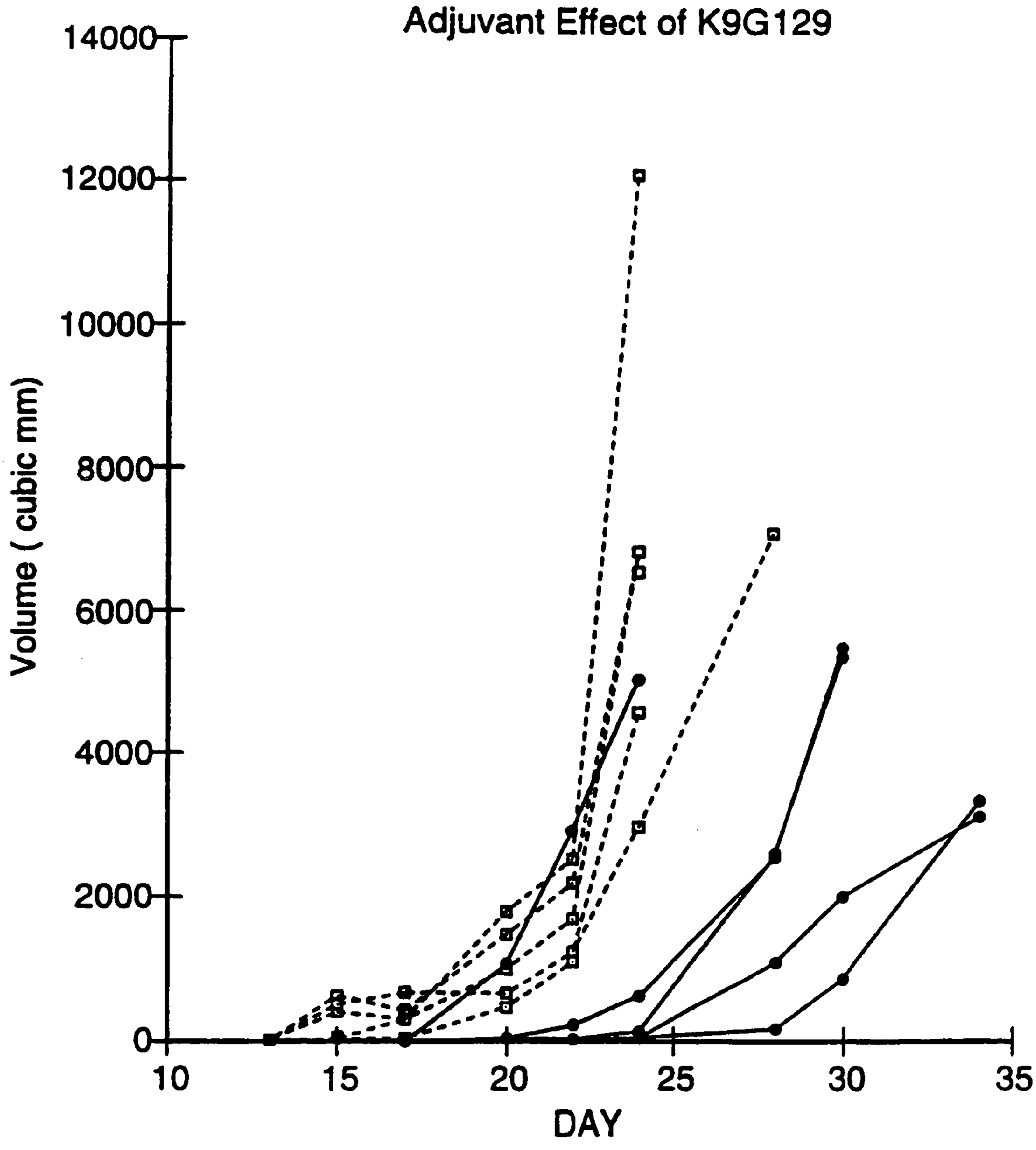
FIG. 8 shows the tumor volumes as at day 30 from two of the six groups of mice plotted versus the number of days after challenge with $10^5$ live melanoma cells. The open boxes with the dashed lines represent the five mice that were immunized with $10^4$ irradiated cells alone (group 2) and the closed circles connected by the solid lines represent the five mice immunized with irradiated cells plus 1 μg of K9G129 (group 3)
Figure 9:
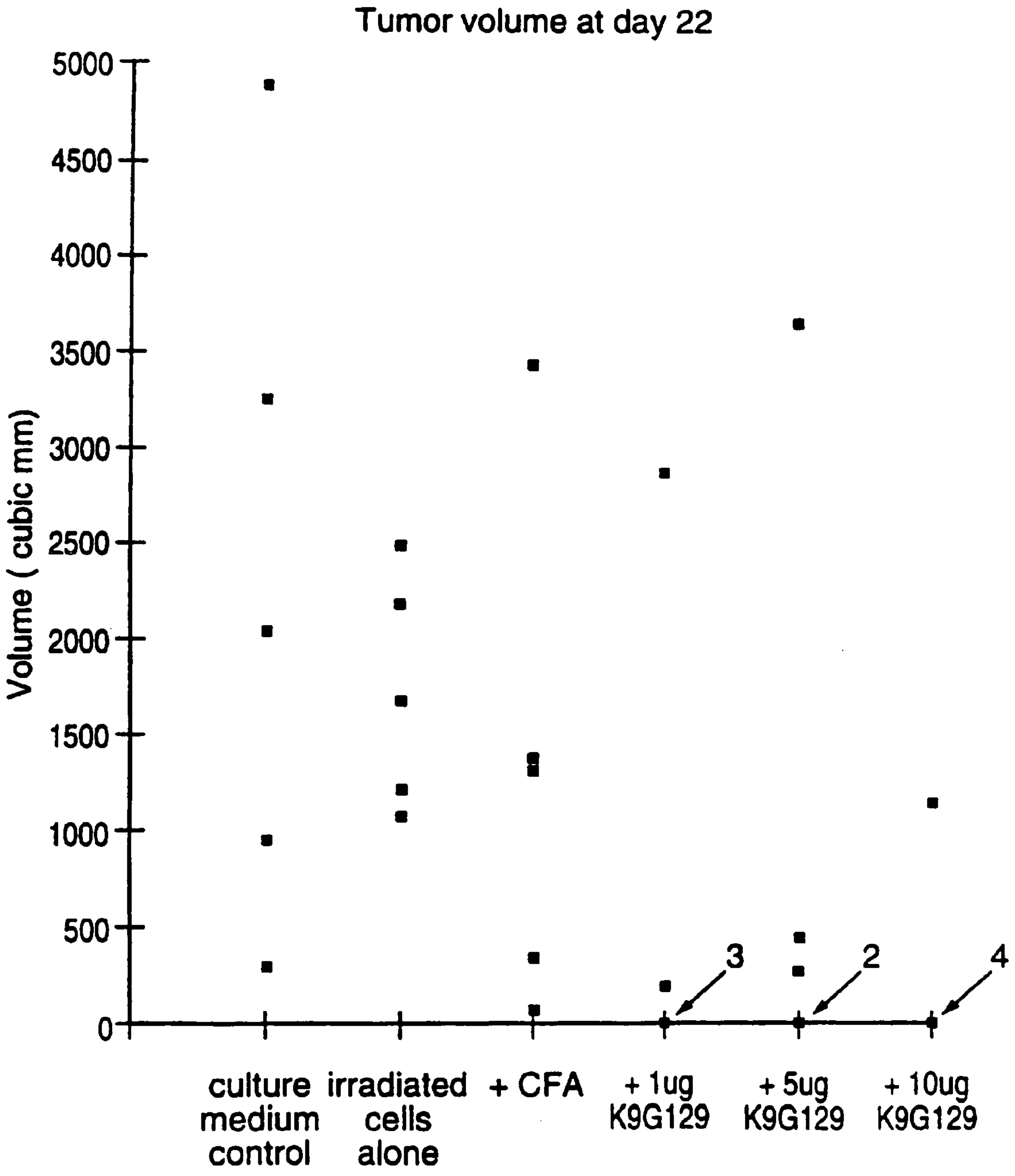
FIG. 9 shows the tumor volumes at day 22. Mice were immunized with cell culture medium as a control and $10^4$ irradiated melanoma cells alone or together with CFA or increasing concentrations of K9G129. The tumor volumes of each of five mice in the six groups are shown 22 days after challenge with $10^5$ live melanoma cells. for the last three groups (mice receiving K9G129), the numbers by the arrows show the number of mice that were free tumors.

Even the lowest concentration of K9G129 used caused a delay in tumor appearance. Four of five mice in group 3 (irradiated cells+1 μg K9G129) had tumors appear after tumors had begun to grow in the mice that had been immunized with irradiated cells alone (group 2) (FIG. 8). The effectiveness of K9G129 in delaying tumor growth is further demonstrated by comparing the tumor volumes of individual mice in the various groups, 22 days after the challenge with live melanoma cells. Tumors are non-existent or their sizes are generally lower in mice that were immunized with irradiated cells and K9G129 than in mice immunized with irradiated cells alone or in conjunction with CFA (FIG. 9).

These results indicate that K9G129 can act as an adjuvant in cancer immunotherapy to increase the immune response towards tumor cells.

Example 11

This Example describes the generation of a Th1 response to an immunogen adjuvanted with the S1(K9G129) *Pertussis* Toxin analogue.

One, of the key factors involved in the potentiation of different immunoglobulin subclasses, including IgE, is the presence of soluble mediators known as cytokines. The control of IgE production is regulated by a variety of cytokines which not only possess direct effector functions such as the induction of immunoglobulin isotype switching, but also act to cross-regulate the production of other cytokines. In the mouse, IL-4 acts not only to induce IgE and IgG1 isotype switching, but also acts to inhibit the secretion of IgM, IgG3, IgG2b and IgG2a (Ref. 48). On the other hand, IFN-γ acts to stimulate the production of IgG2a and IgG3 while inhibiting IgG1, IgG2b and IgE synthesis (Ref. 48).

In an effort to organize and rationalize the multiple and cross-regulatory effects of cytokines, a system to describe the various patterns of cytokine secretion has been described (Ref. 49). Mosmann and Coffman (Ref. 49) defined two distinct subsets of murine $CD4^+$ T cells based on their differential patterns of cytokine secretion. Using long term T cell clones, they were able to show that one group of cells, defined as Th2, secreted IL-4, IL-5 and IL-10 while another group of cells, defined as Th1, secreted IL-2, IFN-γ and TNF-β. These two distinct cytokine profiles were also correlated with immunoglobulin production in that Th1 clones provided help for B lymphocytes to produce IgG2a while Th2 clones promoted the secretion of IgG1 and IgE by B cells (48,50,51). Later work by Romagnani and coworkers demonstrated the existence of these T cell subsets in humans as well (Ref. 52).

Although the initial differentiation of Th1/Th2 cytokine profiles was defined on the basis of in vitro cytokine patterns of individual T cell clones, the definitions have been extended to describe the cytokine phenotypes resulting from immunization or infection (Ref. 48,53). These phenotypes are not as starkly polar as those observed in the original clonal analysis and are defined by a variety of different cytokines. Thus, a Th1 phenotypic response is characterized by a significant increase in Th1-type cytokines (higher ratios of IFN-γ:IL-4) relative to Th2 immune response phenotypes. This classification also extends to the antigen-specific immunoglobin subclass profiles where Th1 phenotypes present as higher IgG2a:IgE ratios relative to Th2 type, responses.

Figure 5:
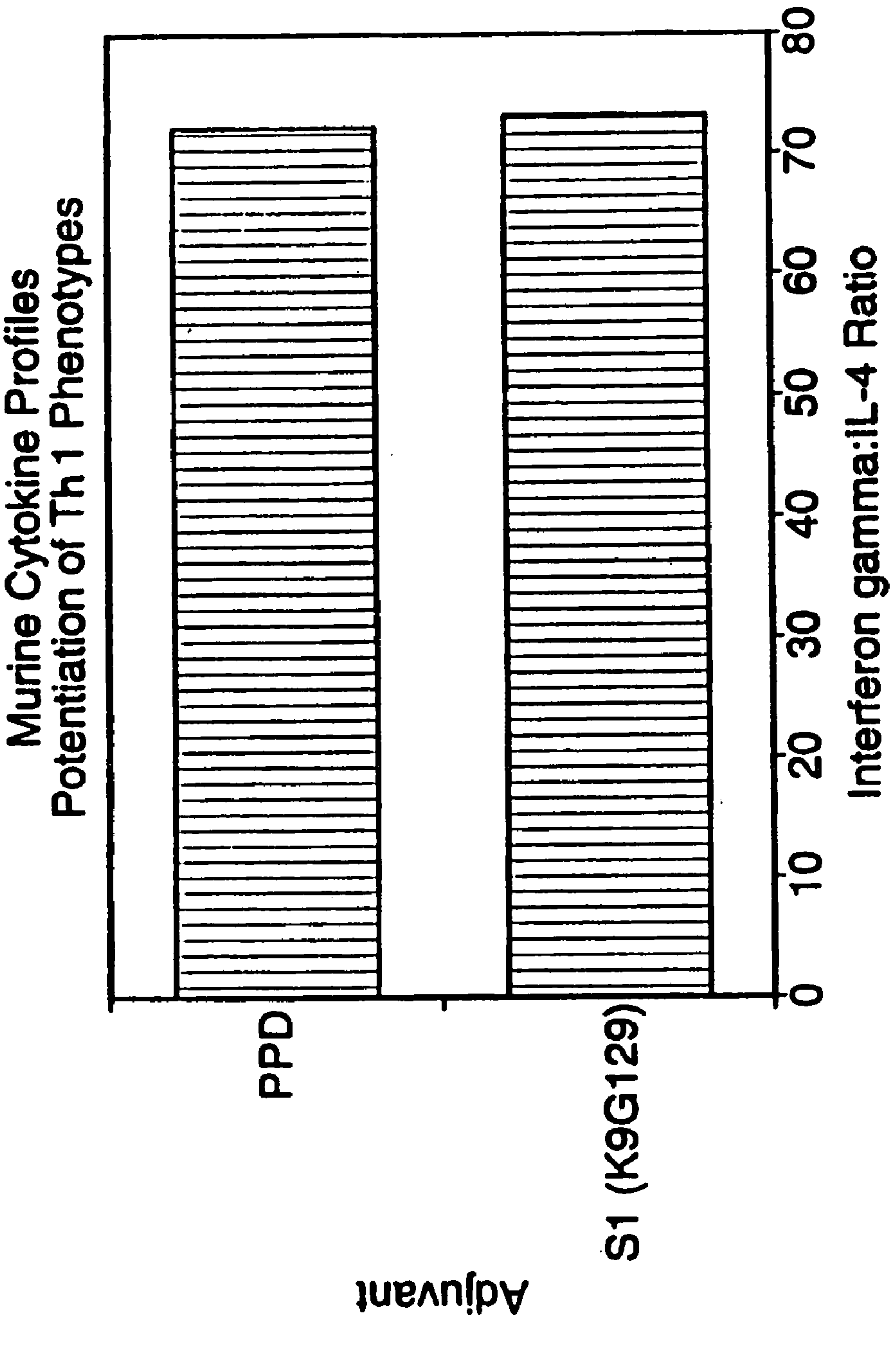
FIG. 5 shows the $T_h1$ and $T_h2$ immune response phenotypes, as determined by cytokine profile in mice immunized with ovalbumin adjuvanted with PPD and genetically detoxified *pertussis* toxin PT (K9G129)

FIG. 5 shows the cytokine profile in mice immunized with ovalbumin and adjuvanted with PPD and PT(K9G129). PPD is an adjuvant that produces a Th1 immune response.

Splenocytes were obtained from mice immunized with ovalbumin along with either S1(K9G129) rPT or PPD as adjuvants. The spleen cells of four mice in each treatment group were pooled and then restimulated in vitro with ovalbumin alone (no adjuvant). The supernatants were then harvested from these cultures and the levels of IFN-γ and IL-4 were determined by EIA. Similar IFN-γ:IL-4 ratios were obtained from cultures derived from mice immunized with either S1(K9G129) or PPD as an adjuvant. As described above, a higher ratio of IFN-γ:IL4 cytokines is characteristic of a Th1 immune response.

Figure 6:
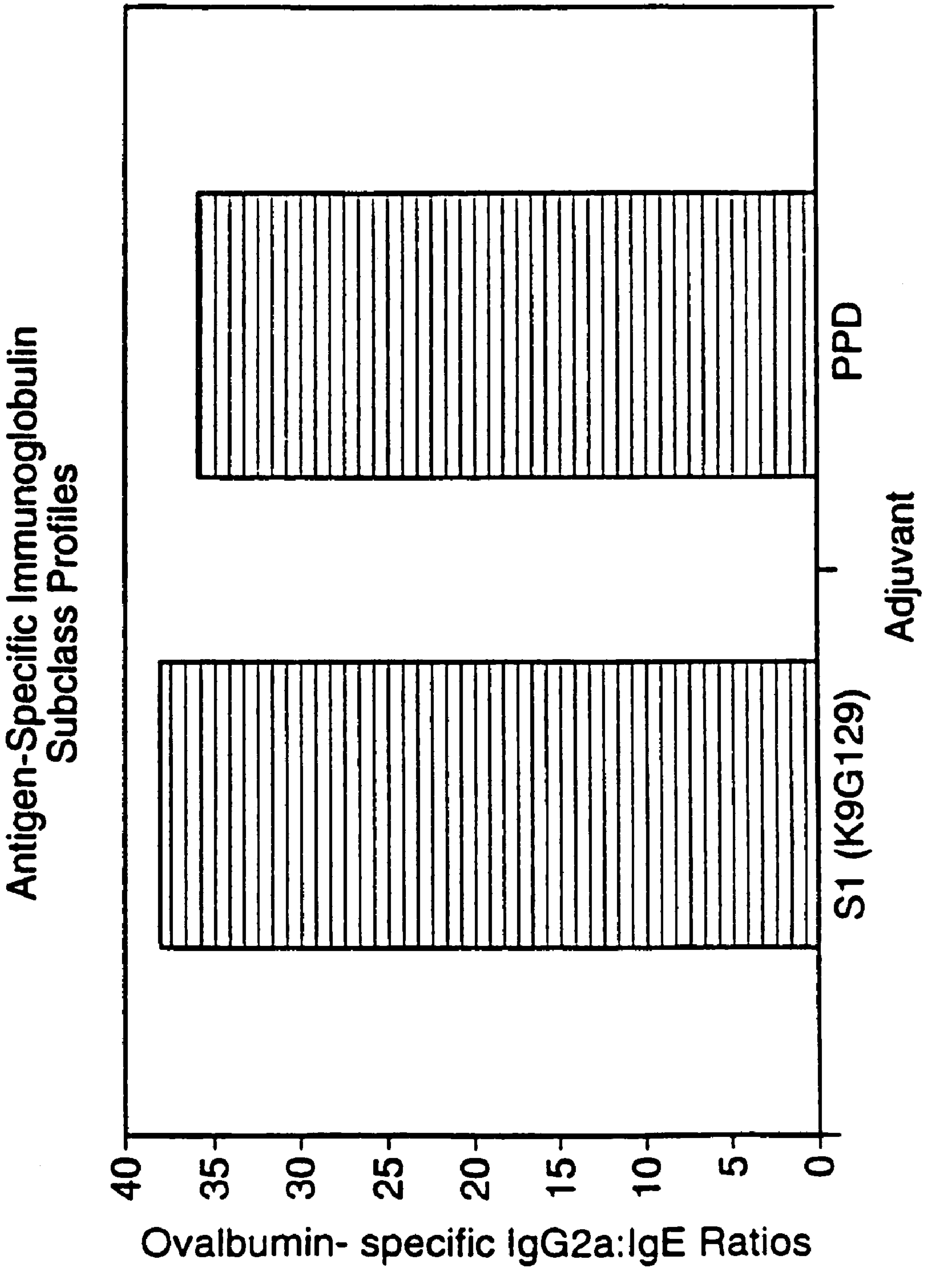
FIG. 6 shows the $T_h1$ and $T_h2$ immune response phenotypes as determined by ovalbumin specific IgG2a and IgGE immunoglobulin profiles in mice immunized with PPD and genetically detoxified *pertussis* toxin, PT (K9GK9)

FIG. 6 shows the ovalbumin-specific IgG2a and IgE responses of BALB/c mice immunized with ovalbumin and either the S1(K9G129) PT analogue or PPD as adjuvants. The bar graph indicates that immunization with the S1(K9G129) PT analogue resulted in ratios of ovalbumin-specific IgG2a:IgE ratios similar to those obtained following immunization with PPD. As described above, a high IgG2a: IgE ratio is characteristic of a Th1 immune response. The results in FIGS. 5 and 6 thus indicate that adjuvanting with PT(K9G129) produces a Th1 immune response in mice.

SUMMARY OF THE DISCLOSURE

In summary of this disclosure, the present invention provides novel immunogenic compositions and methods of immunization in which a genetically-detoxified *pertussis* holotoxin, which may also be immunogenic, is employed as a proteinaceous adjuvant in place of conventional extrinsic adjuvants, particularly alum, to achieve a modulated immune response to a non-*Bordetella* antigen without the adverse side effects of alum. Modifications are possible within the scope of the invention.

TABLE 1a

Mutations introduced into Pertussis Toxin

| Mutation Number | Mutation | |
|---|---|---|
| 1. | ARG$^{9}$ | -> ▲9 |
| 2. | " | -> GLU$^{9}$ |
| 3. | " | -> LYS$^{9}$ |

TABLE 1a-continued

Mutations introduced into Pertussis Toxin

| Mutation Number | Mutation | |
|---|---|---|
| 4. | " | -> HIS$^{9}$ |
| 5. | ARG$^{13}$ | -> ▲13 |
| 6. | " | -> GLU$^{13}$ |
| 7. | ARG$^{9}$–ARG$^{13}$ | -> ▲9–13 |
| 8. | ARG$^{9}$ ARG$^{13}$ | -> GLU$^{9}$ GLU$^{13}$ |
| 9. | ARG$^{58}$ | -> GLU$^{58}$ |
| 10. | ARG$^{57}$ ARG$^{58}$ | -> ▲57▲58 |
| 11. | TRP$^{26}$ | -> ALA$^{26}$ |
| 12. | " | -> CYS$^{26}$ |
| 13. | CYS$^{41}$ | -> ALA$^{41}$ |
| 14. | " | -> SER$^{41}$ |
| 15. | CYS$^{201}$ | -> ALA$^{201}$ |
| 16. | GLU$^{129}$ | -> ▲129 |
| 17. | " | -> GLY$^{129}$ |
| 18. | " | -> GLN$^{129}$ |
| 19. | " | -> ASP$^{129}$ |
| 20. | " | -> ASN$^{129}$ |
| 21. | " | -> LYS$^{129}$ |
| 22. | " | -> ARG$^{129}$ |
| 23. | " | -> HIS$^{129}$ |
| 24. | " | -> PRO$^{129}$ |
| 25. | " | -> CYS$^{129}$ |
| 26. | " | -> GLY$^{129}$ II |
| 27. | " | -> GLN$^{129}$ II |
| 28. | TYR$^{130}$ | -> ▲130 |
| 29. | " | -> PHE$^{130}$ |
| 30. | GLU$^{129}$ TYR$^{130}$ | -> GLY$^{129}$ ALA$^{130}$ |
| 31. | GLU$^{129}$ TYR$^{130}$ | -> GLN$^{129}$ ALA$^{130}$ |
| 32. | GLU$^{129}$ TYR$^{130}$ | -> GLY$^{129}$ PHE$^{130}$ |
| 33. | S3)LYS$^{10}$ | -> GLN$^{10}$ |
| 34. | (S3)TYR$^{92}$ LYS$^{93}$ | -> ASN$^{92}$ ARG$^{93}$ |
| 35. | (S3)LYS$^{105}$ | -> ASN$^{05}$ |
| 36. | CYS$^{41}$ CYS$^{20}$1 | -> ALA$^{41}$ ALA$^{201}$ |
| 37. | CYS$^{41}$ GLU$^{129}$ | -> ALA$^{41}$ GLY$^{129}$ |
| 38. | ARG$^{9}$ GLU$^{129}$ | -> GLU$^{9}$ GLY$^{129}$ II |
| 39. | ARG$^{9}$ GLU$^{129}$ | -> GLU$^{9}$ GLN$^{129}$ II |
| 40. | ARG$^{9}$ GLU$^{129}$ | -> GLU$^{9}$ $^{ARG129}$ |
| 41. | ARG$^{9}$ GLU$^{129}$ TYR$^{130}$ | -> GLU$^{9}$ GLY$^{129}$ ALA$^{130}$ |
| 42. | ARG$^{13}$ GLU$^{129}$ | -> GLU$^{13}$ GLY$^{129}$ II |
| 43. | ARG$^{13}$ GLU$^{129}$ | -> GLU$^{13}$ GLN$^{129}$ II |
| 44. | ARG$^{13}$ GLU$^{129}$ TYR$^{130}$ | -> GLU$^{13}$ GLY$^{129}$ ALA$^{130}$ |
| 45. | ARG$^{9}$ GLU$^{129}$ | -> ▲$^{9}$ GLN$^{129}$ S-2730-1-1 |
| 46. | ARG$^{9}$ GLU$^{129}$ TYR$^{130}$ | -> ▲$^{9}$ GLY$^{129}$ ALA$^{130}$ |
| 47. | ARG$^{13}$ GLU$^{129}$ | -> ▲$^{13}$ GLN$^{129}$ |
| 48. | ARG$^{13}$ GLU$^{129}$ TYR$^{130}$ | -> ▲$^{13}$ GLY$^{129}$ ALA$^{130}$ |
| 49. | GLU$^{129}$ (S3)TYR$^{92}$ LYS$^{93}$ | -> GLY$^{129}$ (S3)ASN$^{92}$ ARG$^{93}$ |
| 50. | Wild Type | |
| 51. | Arg13 | -> Lys13 |
| 52. | Arg58 | -> His58 |
| 53. | Arg58 | -> Lys58 |
| 54. | His35 | -> Ala35 |
| 55. | Glu129 | -> Ser129 |
| 56. | Tyr130 | -> Ser130 |
| 57. | Arg58Glu129 | -> GLu58Gly129 |
| 58. | Arg9Glu129 | -> Lys9Gly129 |
| 59. | Arg9Arg58Glu129 | -> Lys9Glu58Gly129 |
| 60. | (S3) Ile91Tyr92Lys93 | -> Delete |
| 61. | (S2) Thr91Arg92Asn93 | -> Delete |
| 62. | (S1) Glu129/ (S3) Ile91Tyr92Lys93 | -> (S1) Gly129/ S3(91–93) delete |
| 63. | (S1) Arg58Glu129/ S3(91–93) | -> (S1) Glu58Gly129/ S3(91–93) delete |
| 64. | (S1) Arg9Glu129/ S3(91–93) | -> (S1) Lys9Gly129/ S3(91–93) delete |
| 65. | (S1) Arg9Arg58Glu129/ S3(91–93) | -> (S1) Lys9Glu58Gly129 S3(91–93) delete |
| 66. | (S2) Thr91Arg92Asn93/ S3(91–93) | -> S2(91–93) delete S3(91–93) delete |

TABLE 1a-continued

Mutations introduced into Pertussis Toxin

| Mutation Number | Mutation | |
|---|---|---|
| 67. | (S3) TYR$^{82}$ | -> ALA$^{82}$ |
| 68. | (S3) ILE$^{91}$ | -> ▲$^{91}$▲$^{92}$▲$^{93}$ |
| 69. | (S3) TYR$^{102}$TYR$^{103}$ | -> A$^{102}$A$^{103}$ |
| 70. | (S3) LYS$^{105}$ | -> ▲$^{105}$ |
| 71. | (S3) LYS$^{105}$ | -> ALA$^{105}$ |
| 72. | (S3) LYS$^{169}$ | -> ALA$^{169}$ |
| 73. | (S3) TYR$^{82}$LYS$^{169}$ | -> ALA$^{82}$ALA$^{169}$ |
| 74. | (S4) TYR$^{4}$ | -> ALA$^{4}$ |
| 75. | (S4) TYR$^{21}$ | -> ALA$^{21}$ |
| 76. | (S4) LYS$^{54}$LYS$^{57}$ | -> ALA$^{54}$ALA$^{57}$ |
| 77. | (S3) TYR$^{82}$(S4)LYS4$^{54}$LYS$^{57}$ | -> (S3) ALA$^{52}$/ (S4)ALA$^{54}$ALA$^{57}$ |
| 78. | (S1) GLU$^{129}$/(S3)TYR$^{82}$ | -> (S1) GLY$^{129}$/ S3(▲82) |
| 79. | (S1) GLU$^{129}$/S3(ILE$^{91}$TYR$^{92}$LYS$^{93}$) | -> (S1) GLY$^{129}$/ (S3)▲$^{91}$▲$^{92}$▲$^{93}$ |

Notes:
Amino acid numbering corresponds to positions in the native subunits.
All mutations are in subunit S1 unless specified as being in S2, S3 or S4.
II denotes use of an alternative codon.
▲ denotes deleted residue(s).
Wild type refers to PT expressed from the unmutated TOX operon in *B. parapertussis*.

TABLE 1b

In vitro characterization of pertussis toxin analogues obtained from recombinant *B. parapertussis*.

| Mutation Number | Residual Toxicity (%) | ADPR Activity (%) | S1 Epitope |
|---|---|---|---|
| 1. | 0.2 | ND | – |
| 2. | 0.1 | 0.2 | +/– |
| 3. | 0.1 | ND | ++++ |
| 4. | 0.2 | 0.1 | +++ |
| 5. | 0.3 | ND | – |
| 6. | 5.0 | ND | ++++ |
| 7. | 0.4 | 0.1 | – |
| 8. | 0.1 | 0.9 | – |
| 9. | 0.7 | 0.6 | +++ |
| 10. | 0.4 | ND | – |
| 11. | 0.5 | ND | + |
| 12. | 6.0 | ND | ND |
| 13. | 0.3 | 0.4 | – |
| 14. | 1.4 | ND | ND |
| 15. | 0.2 | 0.1 | – |
| 16. | 0.1 | ND | ++ |
| 17. | 0.1 | 0.3 | ++++ |
| 18. | 0.02 | 0.1 | +/– |
| 19. | 0.7 | 2.5 | ++ |
| 20. | 0.1 | 0.3 | ++ |
| 21. | 0.3 | 0.2 | – |
| 22. | 0.1 | ND | – |
| 23. | 0.2 | ND | – |
| 24. | 0.2 | ND | + |
| 25. | 0.4 | ND | – |
| 26. | 0.1 | 0.3 | ++++ |
| 27. | 0.02 | 0.1 | +/– |
| 28. | 0.2 | 0.1 | – |
| 29. | 12.0 | ND | ++++ |
| 30. | 0.2 | 0.6 | – |
| 31. | 0.4 | ND | – |
| 32. | 1.0 | ND | ++++ |
| 33. | 100 | ND | ++++++ |
| 34. | 50 | 100 | ++++ |
| 35. | 20 | ND | ++++ |
| 36. | 0.2 | 0.1 | – |
| 37. | 0.1 | 0.1 | – |
| 38. | 0.1 | 0.1 | – |

TABLE 1b-continued

In vitro characterization of pertussis toxin analogues obtained from recombinant *B. parapertussis*.

| Mutation Number | Residual Toxicity (%) | ADPR Activity (%) | S1 Epitope |
|---|---|---|---|
| 39. | 0.1 | ND | – |
| 40. | 0.1 | ND | – |
| 41. | 0.2 | ND | – |
| 42. | 0.5 | ND | – |
| 43. | 3.0 | ND | – |
| 44. | 0.3 | ND | – |
| 45. | 0.4 | ND | – |
| 46. | 0.2 | 0.1 | – |
| 47. | 0.5 | ND | – |
| 48. | 0.4 | 0.3 | – |
| 49. | 0.2 | 0.1 | ++++ |
| 50. | 100 | 100 | ++++ |
| 51. | 14.0 | | +++++ |
| 52. | 35.0 | | +++++ |
| 53. | 13.0 | | +++++ |
| 54. | 0.2 | | ++ |
| 55. | 0.6 | | +++++ |
| 56. | 29.0 | | ++++ |
| 57. | 0.1 | | ++ |
| 58. | <0.001 | <0.001 | +++ |
| 59. | 0.1 | | + |
| 60. | 12.0 | | +++++ |
| 61. | 100.0 | | +++++ |
| 62. | 0.03 | 0.2 | +++ |
| 63. | 0.1 | | + |
| 64. | 0.1 | | +++ |
| 65. | 0.1 | | + |
| 66. | 10.0 | | + |
| 67. | 7.2 | 96 | ND |
| 68. | 4.6 | 108 | ND |
| 69. | 9.6 | 98 | ND |
| 70. | 8.1 | 57 | ND |
| 71. | 94 | 71 | ND |
| 72. | 102 | 71 | ND |
| 73. | 5.2 | 92 | ND |
| 74. | 46 | 125 | ND |
| 75. | 84 | 91 | ND |
| 76. | 9.6 | 55 | ND |
| 77. | 1.5 | 97 | ND |
| 78. | 0.04 | 0.10 | ND |
| 79. | 0.04 | 0.16 | ND |

Notes:
Residual toxicity is the ratio of the apparent PT concentration determined by the CHO cell clustering assay to the actual concentration of PT mutant determined by ELISA expressed as a percentage.
ADPR activity is the extent of ADP-ribosylation of bovine transducin catalysed by a PT analogue, relative to that catalysed by an equal concentration of wild-type PT, expressed as a percentage.
S1 epitope refers to the expression of an immunodominant S1 epitope recognized by a specific monoclonal antibody PS21 (ATCC HB 10299 deposited Nov. 30, 1989), as compared with the wild-type PT (+++++).
ND denotes not determined.

TABLE 2

Functional amino acid residues in pertussis toxin f r mutation

| Subunit | Residues | Preferred Replacement |
|---|---|---|
| S1 | Phe-23 | Asp or Glu |
| | Ser-48 | Ala |
| | Val-51 | Ile |
| | Gln-127 | Ala or Asp |
| | Leu-131 | Lys or Arg |
| | Gly-199 | Val or Gln |
| | Ala-200 | Ile |
| | Phe-235 | Glu |
| S2 | His-15 | Ala or Thr |
| | Gln-16 | Ala or Thr |
| | Trp-52 | Val |

TABLE 2-continued

Functional amino acid residues in pertussis toxin f r mutation

| Subunit | Residues | Preferred Replacement |
|---|---|---|
| | Glu-66 | Ala or Lys |
| | Asp-81 | Ala or Ser |
| | Leu-82 | Ala or Glu |
| | Lys-83 | Glu |
| | Ser-104 | Ala |
| | Arg-125 | Ala |
| | Ser-147 | Thr |
| | Arg-150 | Ser |
| | Lys-151 | Ser |
| S3 | Gln-15 | Ala or Thr |
| | Gln-16 | Ala or Thr |
| | Tyr-82 | Ala or Val |
| | Arg-83 | Glu |
| | Ser-104 | Ala |
| | Arg-125 | Ala |
| | Arg-150 | Ser |
| | Arg-151 | Ser |
| S4 | Asp-1 | Ala |
| | Tyr-4 | Ala or Val |
| | Gly-60 | Val |
| | Ser-61 | Ala |
| | Glu-65 | Ala |
| | Arg-69 | Ala |
| | Thr-88 | Val |
| | Pro-93 | Ala |
| | Asp-54 | Glu |
| | Thr-51 | Tyr |
| | Thr-55 | Tyr |
| | Gly-58 | Val |
| S5 | Ser-62 | Ala |

TABLE 3

Immunogenicity of the Pertussis toxin component of a DTP acellular vaccine and an acellular DTP vaccine containing a genetically detoxified PT analog

| Vaccine Formulation | Anti-pertussis toxin IgG Reactive titre | Reciprocal CHO cell neutralization titre |
|---|---|---|
| DTP acellular vaccine | 1,363,678 | 50.8 |
| Recombinant acellular vaccine | 1,363,678 | 40.3 |

REFERENCES

1. Bergstrand H., Andersson I., Nystrom I., Pauwels R., Bazin H. (1983) The Non-specific enhancement of allergy. II. Precipitation of anaphylactic in vitro response capacity and serum IgE and IgG2a antibody synthesis in primed but non-responding rats by injection of alum. Allergy 38:247–260
2. Cogne M., Ballet J. J. Schmitt C., Bizzini B. (1985) Total and IgE antibody levels following booster immunization with aluminum adsorbed and nonadsorbed tetanus toxoid in humans. Ann. Allergy 54:148–151
3. Nagel J., Svec D., Waters T., Fireman P. (1977) IgE Synthesis in Man: I. Development of specific IgE antibodies after immunization with Tetanus-Diphtheria (Td) toxoids. J. Immunol. 118:334–341
4. Hedenskog S., Bjorksten B., Blennow M., Granstrom G., Granstrom M. (1989) Immunoglobulin E response to *pertussis* toxin in whooping cough and after immunization with a whole cell and an acellular *pertussis* vaccine. Int. Arch. Allergy Appl. Immunol. 89:156–161.
5. World Health Statistics (1992) immunization coverage. World Health Organization, Geneva, pp. 19–24.
6. Medical Research Council (1951) Br. Med. J. 2:1464–1472.
7. Medical Research Council (1956) Br. Med. J. 2:454–462.
8. Medical Research Council (1959) Br. Med. J. 1:994–1000.
9. Fine P. E., Clarkson J. A. (1987) Reflections on the efficacy of *pertussis* vaccines. Rev. Infect. Dis. 9:866–883.
10. Kanai K. (1980) Japan's experience in *pertussis* epidemiology and vaccination in the past thirty years. Jpn. J. Med. Sci. Biol. 33:107–143.
11. Miller D. L. Alderslade R., Ross E. M. (1982) Whooping cough and whooping cough vaccine: the risks and benefits debate. Epidemiol. Rev. 4:1–24.
12. Romanus V., Jonsell R., Bergquist S. O. (1988) *Pertussis* in Sweden after the cessation of general immunization in 1979. Pediatr. Infect. dis. 6:364–371.
13. Munoz J. J., Arai H., Bergman K., Sadowski P. L. (1981) Biological activities of *crystallin pertussigen* from *Bordetella pertussis*. Infect. Immun. 33:820–826
14. Marwick C. (1988) *Pertussis* vaccines: Trials and Tribulations. JAMA 259:2057–2059.
15. Storsaeter J., Hallander H., Farrington C. P., Olin P., Molby R., Miller E. (1990) Secondary analyses of the efficacy of two acellular *pertussis* vaccines evaluated in a Swedish phase III trial. Vaccine 8:457–461.
16. Loosmore, S. Zealey, G., Cockle S. Boux, H., Chong, P., Yacoob, R. and Klein, M. (1993) Characterization of *pertussis* toxin analogs containing mutations in B-oligomer subunits. Infect. Immun. 61:2316–2324.
17. Burnette W. N., Cieplak W., Smith S. G., Keith J. M. (1989) Effects of mutations on enzyme activity and immunoreactivity of the S1 subunit of *pertussis* toxin. Infect. Immun. 57:3660–3662.
18. Loosmore S., Cockle S., Zealey G., Boux H., Cockle S., Radika K., Fahim R., Zobrist G., Yacoob R. K., Chong P., Yao F. L., Klein M. (1990) Engineering of genetically detoxified *pertussis* toxin analogs for development of a recombinant whooping cough vaccine. Infect. Immun. 58:3653–3662.
19. Nencioni L., Pizza M., Bugnoli M., DeMagistris T., Di Tomasso A., Giovannoni F., Manetti R., Marsili I., Matteucci G., Nucci D., Olivieri R., Pileri P., Presentini R., Villa L., Kreeftenberg J. G., Silvestri S., Tagliaube A., Rappuoli R. (1990) Characterization of generically inactivated *pertussis* toxin mutants: Candidates for a new vaccine against whooping cough. Infect. Immun. 58:1308–1315.
20. Lobet Y., Cieplak W., Mar V. L., Kaljot K. T., Sato H., Keith J. M. (1988) *Pertussis* toxin S1 mutant with reduced enzyme activity and a conserved protective epitope. Science 242:72–74.
21. Pizza M., Covacci A., Bartolini A., Perugini M., Nencioni L., DeMagistris T., Villa L., Nucci D., Manetti R., Bugnoli M., Giovannoni F., Olivieri R., Barbieri J., Sato H., Rappuoli R. (1989) Mutants of *pertussis* toxin suitable for vaccine development. Science 246:497–499.
22. Podda A., Nencioni L., Demagistris M., Di Tomasso A., Bossu P., Nuti S., Pileri P., Peppoloni S., Bugnoli M., Ruggiero P., Marsili I., D'Errico A., Tagliabue A., Rappuoli R. (1990) Metabolic, humoral and cellular responses in adult volunteers immunized with the genetically inactivated *pertussis* toxin mutant PT-9K/129G. J. Exp. Med. 172:861–868.

23. Mills K. H. G., Barnard A., Watkins J., Redhead K. (1993) Cell-mediated immunity to *Bordetella pertussis*: Role of Th1 cells in bacterial clearance in a murine respiratory infection model. Infect. Immun. 61:399–410.

24. Redhead K., Watkins J., Barnard A., Mills. K. H. G. (1993) Effective immunization against *Bordetella pertussis* respiratory infection in mice is dependent on induction of cell-mediated immunity. Infect. Immun. 61:3190–3198.

25. De Magistris M., Romano M., Nuti S., Rappuoli R., Tagliabue A. (1988) Dissecting human T cell responses against *Bordetella* species. J. Exp. Med. 168:1351–1362.

26. Gearing A. J. H., Bird C. R., Redhead K., Thomas M. (1989) Human cellular immune responses to *Bordetella pertussis* infection. FEMS Microbiol. Immunol. 47:205–212.

27. Tomoda T., Ogura H., Kurashige T. (1991) Immune responses to *Bordetella pertussis* infection and vaccination. J. Inf. Dis. 163:559–563.

28. Petersen J. W., Ibsen P. H., Bentzon M. W., Capiau C., Heron I. (1991) The cell mediated and humoral immune response to vaccination with acellular and whole cell *pertussis* vaccine in adult humans. FEMS Microbial. Immunol. 76:279–288.

29. Podda A., DeLuca E., Titone L., Casadel A., Cascio A., Peppoloni S., Volpini G., Marsili I., Nencioni L., Rappuoli R. (1992) Acellular *pertussis* vaccine composed of genetically inactivated *pertussis* toxin: Safety and immunogenicity in 12-to-24 and 2-to-4 month old children. J. Pediatr. 120:680–685.

30. Podda A., Nencioni L., Marsili I., Peppoloni S., Volpini G., Donati D., Di Tommaso A., De Magistris T., Rappuoli R. (1991) Phase I clinical trial of an acellular *pertussis* vaccine composed of genetically detoxified *pertussis* toxin combined with FHA and 69 RD. Vaccine 9:741–745.

31. Nencioni L., Volpini G., Peppoloni S., Bugnoli M., DeMagistris T., Marsili I., Rappuoli R. (1990) Properties of *Pertussis* toxin mutant PT-9K/129G after formaldehyde treatment. Infect. Immun. 59:625–630.

32. Marsili I., Pizza M., Giovannoni F., Volpini G., Bartalini M., Olivieri R., Rappuoli R., Nencioni L. (1992) Cellular *pertussis* vaccine containing a *Bordetella pertussis* strain that produces a nontoxic *pertussis* toxin molecule. Infect. Immun. 60:1150–1155

33. Long S. S., Deforest A., Pennridge Pediatric Associates, Smith D. G., Lazaro C., Wassilak G. F. (1990) Longitudinal study of adverse reactions following Diphtheria-Tetanus-*Pertussis* vaccine in infancy. Pediatrics 85:294–302.

34. Butler N. R., Voyce M. A., Burland W. L., Hilton M. J. Advantages of aluminum hydroxide adsorbed combined diphtheria, tetanus, and *pertussis* vaccines for the immunization of infants. Br. Med. J. 1:663–666.

35. Aprile M. A., Wardlaw A. C. (1966) Aluminum compounds as adjuvants for vaccines and toxoids in man: A review. Can J. Pub. Health 57:343–354.

36. Pineau A., Durand C., Guillard O., Bureau B., Stalder J. (1992) Role of aluminum in skin reactions after diphtheria-tetanus-*pertussis*-poliomyelitis vaccination: An experimental study in rabbits. Toxicology 73:117–125.

37. Goto N., Akama K. (1982) Histopathological studies of reactions in mice injected with aluminum-adsorbed tetanus toxoid. Microbiol. Immunol. 26:1121–1132.

38. Erdohazi M., Newman R. L. (1971) Aluminum hydroxide granuloma. Br. Med. J. 3:621–623

39. Bernier R. H., Frank J. A., Nolan T. F. (1981) Abscesses complicating DTP vaccination. Am. J. Dis. Child. 135: 826–828

40. Cox N. H., Moss C., Forsyth A. (1988) Cutaneous reactions to aluminum in vaccines: an avoidable problem. Lancet ii, 43.

41. Strom J. (1967) Further experience of reactions, especially of a cerebral nature, in conjunction with triple vaccination: A study based on vaccinations in Sweden 1959–1965. Br. Med. J. 4:320–323.

42. Lione A. (1986) More on aluminum in infants. New England J. Med. 314:923

43. Gupta R. K. 7 Sharma S. B., Ahuja S., Saxena S. N. (1987) The effect of aluminum phosphate adjuvant on the potency of *pertussis* vaccine. J. Biol. Stand. 15:99–101.

44. Sar so J. S., Bahrawi W., Witjaksono 14, . . . , Budiarso R. L. P., Brotowasisto B., Dewitt W. R., Gomez C. Z. (1978) A controlled field trial of plain and aluminum hydroxide adsorbed cholera vaccines in Surabaya, Indonesia, during 1973–1975. Bull. WHO 56:619.

45. Collier L. H., Polakoff S., Mortimer J. (1979) Reactions and antibody responses to reinforcing doses of adsorbed and plain tetanus vaccines. Lanct i:1364.

46. Gupta R. K., Relyveld E. H. (1991) Adverse reactions after injection of adsorbed diphtheria-*pertussis*-tetanus (DPT) vaccine are not due only to *pertussis* organisms or *pertussis* components in the vaccine. Vaccine 9:699–702.

47. Granstrom M., Granstrom P., Gillenius P., Askelof P. (1985) Neutralizing antibodies to *pertussis* toxin in whooping cough. J. Infect. Dis. 151:646–649.

48. Mosmann T. R., Schumacher J. H., Street N. F., Budd R., O'Garia A., Fong T., Mond M. W., Moore W. M., Sner A., Fiorentino, D. F. (1991) Diversity of cytokine synthesis and function of mouse CO4 T-cells. Imm. Rev. 123: 219–229/

49. Mosmann T. R., Cherwinski H., Bond H. W., Gredlin A., Coffman R. L. (1986) Two types of murine helper T cell clone, I. Definition according to profiles of cytokine activates and secreted proteins. J. Immunol. 136: 2348–2357.

50. Mosmann T. R., Coffman R. L. (1989) $T_h1$ and $T_h2$ cells: Different patterns of lymphokine secretion lead to different functional properties. Ann. Rev. Immunol. 7:145–173.

51. Coffman R. L., Seymour B. W. P., Debman D. A., Hivaki D. D., Christiansen J. A., Shrader B. chervinski H. M., Savelkoul H. P. J., Finkelman F. D., Bond M. W., Mosmann T. R. (1988) The role of helper T cell products in mouse B-cell differentiation and isotype regulation. Immunol. Rev. 102:5–28.

52. Romagnani S. (1991) Human $T_h1$ and $T_h2$ subsets: Doubt no More. Immunol. Today 12: 256–257.

53. Coffman R. L., Varkila K., Scott P., Chatelain R. (1991) Role of cytokines in the differentiation of CD4 T cell subsets in vno. Imm. Rev. 123:189–207.

54. Bystryn J-C, Bart R. S., Livingston P., Kopf A. W. (1974) Growth and immunogenicity of murine B-16 melanoma. Journal of Investigative Dermatology, 63, 369–373.

We claim:

1. An immunogenic composition comprising:

a genetically detoxified-*pertussis* holotoxin, and at least one, non-*Bordetella* antigen comprising inactivated tumour cells or membrane fraction thereof wherein said genetically detoxified-*pertussis* holotoxin is present in an amount sufficient to modulate an immune response to said non-*Bordetella* antigen in the absence of extrinsic adjuvant.

2. The composition of claim 1 wherein said cells are inactivated by irradiation.

3. The composition of claim 1 wherein at least one amino acid is removed or replaced in said genetically detoxified-*pertussis* holotoxin.

4. The composition of claim 3 wherein multiple amino acids are removed or replaced in said genetically detoxified-*pertussis* holotoxin.

5. The composition of claim 3 or 4 wherein said at least one amino acid is selected from the group consisting of (SI) ARG9, ARG13, TRP26, ARG58, and GLU129.

6. The composition of claim 4 wherein said multiple amino acids are (SI) ARG9, GLU129.

7. The composition of claim 6 wherein said multiple amino acids are (SI) ARG9 to LYS9 and GLU129 to GLY129.

8. A method of obtaining a modulated immune response to an antigen in a host comprising:

administering at least one, non-*Bordetella* antigen to said host, said antigen comprising inactivated tumour cells or a membrane fraction thereof, and a genetically detoxified *pertussis* holotoxin in an amount sufficient to modulate an immune response to said non-*Bordetella* antigen in the absence of extrinsic adjuvant.

9. The method of claim 8 wherein said host is a human.

10. The method of claim 8 wherein said cells are inactivated by irradiation.

* * * * *